United States Patent
Kantoff et al.

(10) Patent No.: US 11,214,837 B2
(45) Date of Patent: *Jan. 4, 2022

(54) METHODS FOR PREDICTING LIKELIHOOD OF RESPONDING TO TREATMENT

(71) Applicant: Dana-Farber Cancer Institute, Inc., Boston, MA (US)

(72) Inventors: Philip W. Kantoff, Brookline, MA (US); Ming Yang, Boston, MA (US); Gwo-Shu Mary Lee, Newton, MA (US); Tong Sun, Newton, MA (US); Wanling Xie, Newton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 182 days.

This patent is subject to a terminal disclaimer.

(21) Appl. No.: 16/299,955

(22) Filed: Mar. 12, 2019

(65) Prior Publication Data

US 2019/0284634 A1     Sep. 19, 2019

Related U.S. Application Data

(63) Continuation of application No. 13/574,001, filed as application No. PCT/US2011/024450 on Feb. 11, 2011, now Pat. No. 10,273,544.

(60) Provisional application No. 61/303,573, filed on Feb. 11, 2010.

(51) Int. Cl.
*C12Q 1/6886*     (2018.01)

(52) U.S. Cl.
CPC ..... *C12Q 1/6886* (2013.01); *C12Q 2600/106* (2013.01); *C12Q 2600/156* (2013.01); *C12Q 2600/172* (2013.01)

(58) Field of Classification Search
CPC ........ C12Q 2600/106; C12Q 2600/156; C12Q 2600/172
See application file for complete search history.

(56) References Cited

U.S. PATENT DOCUMENTS

| | | |
|---|---|---|
| 4,499,052 A | 2/1985 | Fulwyler |
| 5,028,545 A | 7/1991 | Soini |
| 5,427,779 A | 6/1995 | Elsner et al. |
| 5,451,683 A | 9/1995 | Barrett et al. |
| 5,733,729 A | 3/1998 | Lipshutz et al. |
| 5,770,722 A | 6/1998 | Lockhart et al. |
| 5,871,928 A | 2/1999 | Fodor et al. |
| 5,902,723 A | 5/1999 | Dower et al. |
| 5,981,180 A | 11/1999 | Chandler et al. |
| 6,197,599 B1 | 3/2001 | Chin et al. |

(Continued)

FOREIGN PATENT DOCUMENTS

| | | |
|---|---|---|
| EP | 1234058 | 8/2002 |
| WO | WO 1998/20019 | 5/1998 |

(Continued)

OTHER PUBLICATIONS

Cole et al., "The EBV-Hybridoma Technique and Its Application To Human Lung Cancer," Monoclonal Antibodies and Cancer Therapy, 198.3, pp. 77-96.

(Continued)

*Primary Examiner* — Diana B Johannsen

(74) *Attorney, Agent, or Firm* — Fish & Richardson P.C.

(57) ABSTRACT

The disclosure provides materials and methods related to using biomarkers for prediction of duration of response to prostate cancer treatment and for treating prostate cancer.

22 Claims, 7 Drawing Sheets

Specification includes a Sequence Listing.

(56) References Cited

U.S. PATENT DOCUMENTS

| | | | |
|---|---|---|---|
| 6,410,231 | B1 | 6/2002 | Arnold et al. |
| 6,916,661 | B2 | 7/2005 | Chandler et al. |
| 10,273,544 | B2 | 4/2019 | Kantoff et al. |
| 2003/0059813 | A1 | 3/2003 | Arnold et al. |
| 2004/0075907 | A1 | 4/2004 | Moon et al. |
| 2004/0125424 | A1 | 7/2004 | Moon et al. |
| 2004/0126875 | A1 | 7/2004 | Putnam et al. |
| 2004/0130761 | A1 | 7/2004 | Moon et al. |
| 2004/0130786 | A1 | 7/2004 | Putnam et al. |
| 2004/0132205 | A1 | 7/2004 | Moon et al. |
| 2004/0179267 | A1 | 9/2004 | Moon et al. |
| 2006/0008823 | A1 | 1/2006 | Kemp et al. |
| 2010/0143909 | A1 | 6/2010 | Okada et al. |
| 2010/0317726 | A1 | 12/2010 | Figg et al. |
| 2013/0095481 | A1 | 4/2013 | Kantoff et al. |

FOREIGN PATENT DOCUMENTS

| | | |
|---|---|---|
| WO | WO 1999/57318 | 11/1999 |
| WO | WO 2001/38580 | 5/2001 |
| WO | WO 2008066002 | 6/2008 |
| WO | WO 2008086002 | 7/2008 |

OTHER PUBLICATIONS

Cote et al., "Generation of human monoclonal antibodies reactive with cellular antigens." Proc. Natl. Acad. Sci USA, Apr. 1983, 80(7):2026-30.

Hacia et al., "Detection of heterozygous mutations in BRCA1 using high density oligonucleotide arrays and two-colour fluorescence analysis." Nature Genet., Dec. 1996, 14(4):441-447.

Huse et al., "Generation of a large combinatorial library of the immunoglobulin repertoire in phage lambda," Science, Dec. 1989, 246(4935):1275-81.

Kohler et al., "Continuous cultures of fused cells secreting antibody of predefined specificity," Nature, Aug. 1975, 256(5517):495-7.

Kozbor et al., "The production of monoclonal antibodies from human lymphocytes." Immunology Today, Mar. 1983, 4(3):72-9.

Lamy et al., "Genotyping and annotation ot Affymetrix SNP arrays," Nucleic Acids Research, Sep. 2006, 34(14):e100, 9 pages.

Mougey et al., "Absorption of Montelukast is Transporter Mediated: a Common Variant of OATP2B1 is Associated with Reduced Plasma Concentrations and Poor Response," Pharmacogenetic Genomics, Feb. 2009, 19(2):129-138.

Nelson et al., "Prostate cancer," N Engl J Med., Jul. 2003. 349(4):366-81.

Oh et al., "Development of an integrated prostate cancer research information system," Clin Genitourin Cancer, Jun. 2006, 5(1):61-66.

PCT International Search Report and Written Opinion in International Appln. No. PCT/US2011/024450, dated Mar. 29, 2011, 8 pages.

Pizzagalli et al., "Identification of steroid sulfate transport processes in the human mammary gland," J Clin Endocrinol Metab., Aug. 2003, 88(8):3902-3912.

Schafer et al., "DNA Variation and the Future of Human Genetics." Nat. Biotechnol., Jan. 1998, 16(1):33-39.

Stoneking et al., "Population variation of human mtDNA control region sequences detected by enzymatic amplification and sequence-specific oligonucleotide probes." Am. J Hum. Genet., Feb. 1991, 48(2):370-382.

Yang et al., "Genetic variations in SLC02B1 and SLC01 83 and the efficacy of androgen-deprivation therapy in prostate cancer patients," American Society of Clinical Oncology, 2010 Genitourinary Cancers Symposium, 2010, 3 pages.

U.S. Appl. No. 13/574,001, 2013/0095481, U.S. Pat. No. 10,273,544, filed Oct. 10, 2012, Kantoff et al.

De Bakker et al. *Transferability of tag SNPs in genetic association studies in multiple populations*, Nat Genet. 38(11):1298-1303 (Oct. 2006).

Feldman and Feldman, *The development of androgen-independent prostate cancer*, Nat Rev Cancer 1(1):34-45 (Oct. 2001).

Hagenbuch and Meier, *Organic anion transporting polypeptides of the OATP/ SLC21 family: phylogenetic classification as OATP/ SLCO superfamily, new nomenclature and molecular/functional properties*, Pflugers Arch. 447(5):653-665 (Feb. 2004).

Hamada, A. et al. *Effect of SLCO1B3 haplotype on testosterone transport and clinical outcome in caucasian patients with androgen-independent prostatic cancer*, Clin Cancer Research 14(11):3312 (Jun. 2008).

International Preliminary Report on Patentability, dated Aug. 14, 2012, which issued in corresponding International Application No. PCT/US2011/024450 (8 pages).

International Search Report, dated Apr. 14, 2011, which issued in corresponding International Application Serial No. PCT/US2011/024450 (2 pages).

Letschert et al., *Mutations in the SLCO1B3 gene affecting the substrate specificity of the hepatocellular uptake transporter OATP1B3 (OATP8)*, Pharmacogenetics, 14(7):441-452 (Jul. 2004).

Lubomirov, R. et al., *Supplementary Table S2* of Pharmacogenetics and Genomics 20:217 (Jan. 2010).

Lubomirov, R. et al. *ADME pharmacogenetics: investigation of the pharmacokinetics of the antiretroviral agent lopinavir coformulated with ritonavir*, Pharmacogenetics and Genomics 20:217-230 (Jan. 2010).

Mougey et al., *Absorption of Montelukastis Transporter Mediated: a Common Variant of OATP2B1 is Associated with Reduced Plasma Concentrations and Poor Response*, Pharmacogenetic Genomics, 19(2):129-138 [online]. Feb. 2009, [retrieved on Mar. 28, 2011], Retrieved from the internet: <URL:http://www.ncblnlm.nih.gov/Dpmc/articles/PMC2641 037/pdf/nihms89874.pdf]; p. 1-19.

Myakishev et al. *High-throughput SNP genotyping by allele-specific PCR with universal energy-transfer-labeled primers*, Genome 11(1):163-169 (Jan. 2001).

Prince et al. *Robust and accurate single nucleotide polymorphism genotyping by dynamic allele-specific hybridization (DASH): design criteria and assay validation*, Genome Res. 11(1):152-162 (Jan. 2001).

Ross et al., *Efficacy of androgen deprivation therapy (ADT) in patients with advanced prostate cancer: association between Gleason score, prostate-specific antigen level, and prior ADT exposure with duration of APT effect*, Cancer 112(6):1247-53 (Mar. 2008).

Ross et al., *Inherited variation in the androgen pathway is associated with the efficacy of androgen-deprivation therapy in men with prostate cancer*, J Clin Oncol. 26(6):842-847 (Feb. 2008).

Scher and Sawyers, *Biology of progressive, castration-resistant prostate cancer: directed therapies targeting the androgen-receptor signaling axis*, J Clin Oncol. 23(32):8253-8261 (Nov. 2005).

Schwabedissen et al., *Hepatic OATP1B Transporters and Nuclear Receptors PXR and CAR: Interplay. Regulation of Drug Disposition Genes, and Single Nucleotide Polymorphisms*, Molecular Pharmaceutics, 6(6):1644-1661 (2009).

Smith et al., *Role of the liver-specific transporters OATP1B1 and OATP1B3 in governing drug elimination*, Expert Opin Drug Metab Toxicol. 1(3):429-445 (Oct. 2005).

Tamai et al., *Molecular identification and characterization of novel members of the human organic anion transporter (OATP) family*, Biochem Biophys Res Commun. 273(1):251-260 (Jun. 2000).

Underhill et al. *Detection of numerous Y chromosome biallelic polymorphisms by denaturing high-performance liquid chromatography*, Genome Res. 7(10):996-1005 (Oct. 1997).

Yang et al., *Genetic variations in SLCO2B1 and SLCO1 83 and the efficacy of androgen-deprivation therapy in prostate cancer patients*, 2010 Genitourinary Cancers Symposium [online], Mar. 2010 [retrieved on Mar. 25, 2011], Retrieved from the internet: <URL:http://www.asco.org/ASCOv21Meetings/Abstracts? D &vmview=abst_detail_view&conftD= 73&abstr ac!ID=30829]; p. 3.

METHODS FOR PREDICTING LIKELIHOOD OF RESPONDING TO TREATMENT

CROSS REFERENCE TO PRIOR APPLICATIONS

This application is a Continuation of U.S. patent application Ser. No. 13/574,001, filed Oct. 10, 2012 (now U.S. Pat. No. 10,273,544) which is a U.S. National Phase application under 35 U.S.C. § 371 of International Patent Application No. PCT/US2011/024450, filed Feb. 11, 2011, and claims the benefit of U.S. Provisional Patent Application No. 61/303,573, filed Feb. 11, 2010, both of which are incorporated by reference herein in their entirety. The International Application published in English on Aug. 18, 2011 as WO 2011/100503 under PCT Article 21(2).

TECHNICAL FIELD

This invention relates to materials and methods for assessing the likelihood of a prostate cancer patient responding to treatment, and in particular, treatment with androgen deprivation therapy, ketoconazole, or abiraterone, as well as methods for treating patients with prostate cancer.

BACKGROUND

Prostate cancer (CaP) is the most commonly diagnosed non-cutaneous cancer in men and a leading cause of morbidity and mortality. Androgens and the androgen receptor (AR) participate in the development of CaP. Androgen deprivation therapy (ADT), which suppresses testicular androgen production (via orchiectomy or luteinizing hormone-releasing hormone agonists), is the most effective systemic therapy for patients with hormone-sensitive CaP (HSPC). Ross et al., *Cancer* 112:1247-53 (2008); and Ross et al., *J Clin Oncol.* 26:842-847 (2008). Unfortunately, most HSPCs eventually become resistant to ADT and progress to castration resistant CaP (CRPC). CRPC proliferates despite castrate levels of serum testosterone and is usually fatal. Feldman and Feldman, *Nat Rev Cancer* 1,34-45 (2001); Nelson et al., *N Engl J Med.* July 24; 349(4):366-81 (2003); and Scher and Sawyers, *J Clin Oncol.* 23:8253-8261 (2005). Thus, there is a need for methods in which response to ADT can be assessed.

SUMMARY

This invention is based on the discovery that single nucleotide polymorphisms (SNPs) in the SLCO2B1 gene, alone or in combination with SNPs in the SLCO1B3 gene, can be used as biomarkers to predict the duration of response of a patient having prostate cancer to respond to therapy, including androgen deprivation therapy (ADT), ketoconazole therapy, or abiraterone therapy. Such knowledge may modify the way these treatments are used.

In one aspect, this document features a method of predicting the likelihood of a subject (e.g., human) having prostate cancer to respond to a treatment, wherein the treatment is selected from the group consisting of ADT, ketoconazole treatment, and abiraterone treatment. For example, the treatment can be ADT. The method includes providing a biological sample (e.g., a blood sample such as peripheral blood sample or tissue sample such as a mucosal scraping sample of the lining of the mouth or a prostate tissue sample) from the subject; detecting in the biological sample the presence or absence of two or more SCLO2B1 SNP genotypes selected from the group consisting of rs12422149 (GG), rs1789693 (TT), and rs1077858 (AG/GG); and classifying the subject as being likely to respond to the treatment based on the absence of two or more of the SNP genotypes, or classifying the subject as not being likely to respond to the treatment based on the presence of two or more of the SNP genotypes. For example, the subject can be classified as being likely to respond to the treatment for a longer duration of time based on the absence of two or more of the SNP genotypes, or can be classified as being likely to respond to the treatment for a shorter duration of time based on the presence of two or more of the SNP genotypes. That is, subjects that do not contain two or more of the SNP genotypes are predicted to respond to the therapy for a longer duration of time relative to subjects having two or more of the SNP genotypes. The method can include detecting the presence or absence of rs12422149 (GG), rs1789693 (TT), and rs1077858 (AG/GG).

The method further can include detecting the presence or absence of SCLO1B3 SNP genotype rs4149117 (GT/TT) in the biological sample, wherein the absence of the SCLO1B3 genotype and the absence of the rs12422149 (GG), rs1789693 (TT), and rs1077858 (AG/GG) genotypes further indicates the subject is likely to respond to the treatment (e.g., for a longer duration of time than a subject having the rs12422149 (GG), rs1789693 (TT), and rs1077858 (AG/GG) genotypes).

The method further can include detecting the presence or absence of SCLO1B3 SNP genotype rs4149117 (GT/TT) in the biological sample, wherein the presence of the SCLO1B3 genotype and the presence of the rs12422149 (GG), rs1789693 (TT), and rs1077858 (AG/GG) genotypes further indicates the subject is not likely to respond to the treatment (e.g., for as long of a duration as a subject that does not have the rs12422149 (GG), rs1789693 (TT), and rs1077858 (AG/GG) genotypes).

Methods described herein further can include creating a record indicating the subject is likely to respond to the treatment for a longer duration of time based on the absence of two or more of the SNP genotypes, or indicating the subject is likely to respond to the treatment for a shorter duration of time based on the presence of two or more of the SNP genotypes. The record can be created on a computer readable medium.

This document also features a method of predicting the likelihood of a human subject having prostate cancer to respond to a treatment, wherein the treatment is selected from the group consisting of ADT, ketoconazole treatment, and abiraterone treatment. The method includes providing a biological sample from the human subject; and determining the nucleotide present at each of three single nucleotide polymorphism (SNP) sites in the biological sample, wherein the SNP sites are rs12422149, rs1789693, and rs1077858, wherein the presence of an A at each SNP site is indicative of an increased likelihood of the subject to respond to the treatment for a longer duration of time as compared with a human subject having a G at SNP sites rs12422149 and rs1077858, and a T at SNP site rs1789693.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2A is a bar graph of SLCO2B1 mRNA levels in mock transfected LNCaP cells and LNCaP cells transfected with different SLCO2B1 variants. All mRNA levels were analyzed by Quantitative RT-PCR and normalized by the expression level of GAPDH. Values represent the fold differences relative to those in mock transfected cells, which were set as 1.0. FIG. 2B is a graph of DHEAS uptake over time. FIG. 2C is a graph of the kinetics of DHEAS uptake (Significant differences were observed among 3 groups, P<0.05). Mock, LNCaP transfected with pCMV6-XL4 vector; SLCO2B1-Gln, LNCaP transiently transfected with pCMV-SLCO-312Gln; SLCO2B1-Arg, LNCaP transiently transfected with pCMV-SLCO-312Arg. All the experiments were repeated in triplex.

FIGS. 3A-3D are bar graphs of the quantitative RT-PCR analysis of expression levels of PSA and AR in various LNCaP and LAPC-4 cell lines with or without DHEAS. In all experiments, the relative expression levels of PSA and AR in each sample were normalized by the expression level of GAPDH. Values represent the fold differences relative to those in mock transfected cells without any drug treatment, which were set as 1.0. FIGS. 3E and 3F are graphs of cell growth based on the WST-1 assay. Solid lines and broken lines represent cells cultured in the presence or absence, respectively, of DHEAS. Triplicate experiments were performed for each set. Points, mean (n=3); bars, SD. Mock refers to cells transfected with pCMV6-XL4 vector; SLCO2B1-Gln refers to cells transfected with pCMV-SLCO-312Gln; SLCO2B1-Arg refers to cells transfected with pCMV-SLCO-312Arg plasmid.

Like reference symbols in the various drawings indicate like elements.

DETAILED DESCRIPTION

Figure 1A:
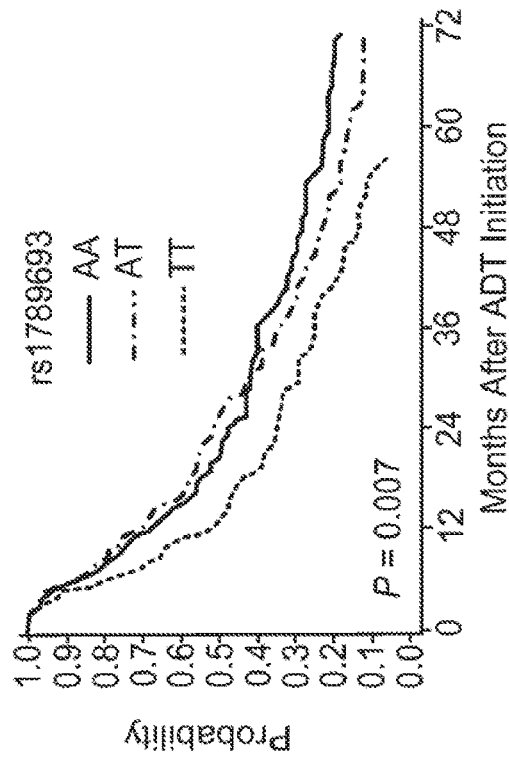
FIGS. 1A-1D are Kaplan-Meier curves of time to progression during androgen deprivation therapy, stratified by: genotype at rs12422149 (FIG. 1A); genotype at rs1789693 (FIG. 1B); genotype at rs1077858 (FIG. 1C); and ≤1, 2, or 3 unfavorable genotype(s) of the three SLCO2B1 SNPs (FIG. 1D).
Figure 1B:
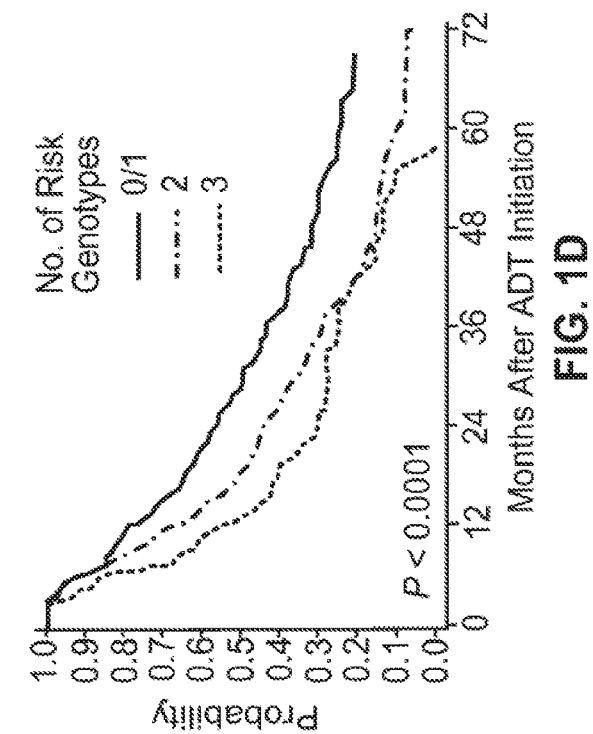
Figure 1C:
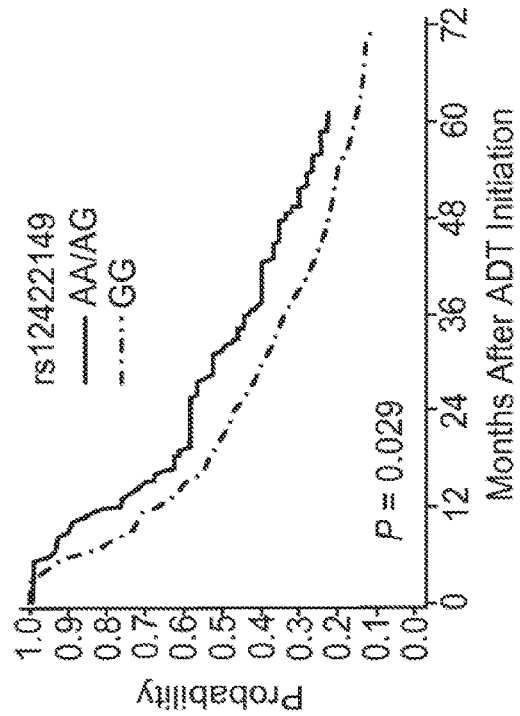

In general, this document provides methods and compositions (e.g., nucleic acid arrays and kits) for predicting the response of a subject (such as a human patient) to therapies that reduce activity or amount of testosterone available. Non-limiting examples of such therapies include ADT, ketoconazole, abiraterone, or aminoglutethimide therapy. ADT refers to treatment to reduce the amount of available testosterone, and can include orchiectomy or treatment with luteinizing hormone releasing hormone (LHRH) agonists or analogs such that the release of LHRH is blocked. Non-limiting examples of LHRH agonists and analogs include leuprolide acetate (ELIGARD®, LUPRON®, and VIADUR™), goserelin acetate (ZOLADEX®), and triptorelin (TRELSTAR®, DECAPEPTYL®, and GONAPEPTYL®). In some embodiments, ADT can include treatment with an anti-androgen receptor antagonist such as bicalutamide (CASODEX®), flutamide (EULEXIN®), or nilutamide (NILANDRON®). Ketoconazole (Nizoral®), abiraterone, and aminoglutethimide are used to block production of testosterone precursors from the adrenal gland and prostate cancer tissue.

This document also provides predictive biomarkers (e.g., SNP genotypes) to identify those subjects for whom administering ADT, ketoconazole, or abiraterone therapy is likely to be effective or ineffective. Such biomarkers, compositions, and methods are useful in selecting appropriate therapeutic modalities for subjects suffering from prostate cancer.

As described herein, a prostate cancer patient's SLCO2B1 genotype, or the SLCO2B1 genotype in combination with the patient's SLCOB3 genotype can be used as a prognostic tool for response during ADT, ketoconazole therapy, or abiraterone therapy. SLCO2B1 and SLCO2B3 are part of a superfamily of organic anion transporting polypeptides encoded by SLCO genes (also known as OATP) that mediate the sodium-independent uptake of a wide variety of endogenous compounds and drugs into cells. SLCO2B1 is expressed in a broad range of tissues and mediates the transport of natural steroid conjugates, such as dehydroepiandrosterone (DHEA), the sulfated form of DHEA (DHEAS), and estrone-3-sulfate (E3S). See Hagenbuch and Meier, *Pflugers Arch.* 447:653-665 (2004); Tamai et al., *Biochem Biophys Res Commun.* 273:251-260 (2000); and Pizzagalli et al., *J Clin Endocrinol Metab.* 88:3902-3912 (2003). SLCO1B3 is involved in the uptake of several hormones including testosterone, and is mainly expressed in liver and various types of cancer cells. See Hamada et al,. *Clin Cancer Res.* 14:3312-3318 (2008); Smith et al., *Expert Opin Drug Metab Toxicol.* 1:429-445 (2005); and Letschert et al., *Pharmacogenetics.* 14:441-452 (2004).

Methods for Assessing Duration of Response to Treatment

Methods described herein can be used for assessing a subject's likelihood of responding to a treatment and can include, for example, testing a biological sample obtained from a subject to determine whether the sample contains one or more biomarkers indicating the duration of time the subject is likely to respond to a treatment. Any suitable biological sample can be used. For example, a biological sample can be a specimen obtained from a male subject (e.g., a mammal such as a human, mouse, rat, pig, guinea pig, cow, monkey, or ape) or can be derived from such a subject. For example, a sample can be a tissue section (prostate tissue biopsy or mucosal scrapings of the lining of the mouth), or cells that are placed in or adapted to tissue culture. A biological sample also can be a biological fluid such as urine, blood, plasma, serum, saliva, tears, or mucus, or such a sample absorbed onto a paper or polymer substrate. A biological sample can be further fractionated, if desired, to a fraction containing particular cell types. In some embodiments, a sample can be a combination of samples from a subject (e.g., a combination of a tissue and fluid sample).

For example, the methods provided herein can be used to predict, based on a biomarker, the length of time a subject having prostate cancer (e.g., a human patient) is likely to respond to ADT, ketoconazole, or abiraterone treatment. A biomarker can be a SNP from the SLCO2B1 gene (e.g., rs12422149, rs1789693, or rs1077858, where the SNP is identified by reference SNP ("rs") followed by the National Center for Biotechnology Information (NCBI) SNP identification number). In some embodiments, a biomarker can be two or three SNPs from the SLCO2B1 gene. In some embodiments, a biomarker can be two or three SNPs from the SLCO2B1 gene and a SNP from the SLCO1B3 gene (e.g., rs4149117 or rs7311358). Nucleotide sequence variants such as SNPs can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al. (1995) *Nat. Biotechnol.* 15:33-39), denaturing high performance liquid chromatography (DHPLC, Underhill et al. (1997) *Genome Res.* 7:996-1005), infrared matrix-assisted laser desorption/ionization (IR-MALDI) mass spectrometry (WO 99/57318), and combinations of such methods.

Genomic DNA generally is used in the analysis of nucleotide sequence variants, although mRNA also can be used. Genomic DNA is typically extracted from a biological sample such as a peripheral blood sample, but can be extracted from other biological samples, including tissues (e.g., mucosal scrapings of the lining of the mouth or from prostate tissue). Routine methods can be used to extract genomic DNA from a blood or tissue sample, including, for example, phenol extraction. Alternatively, genomic DNA can be extracted with kits such as the QIAAMP® Tissue Kit (Qiagen, Chatsworth, Calif.) and the WIZARD® Genomic DNA purification kit (Promega).

An amplification step is typically, but not necessarily, performed before proceeding with the detection method. For example, exons or introns of a gene can be amplified and then directly sequenced. Dye primer sequencing can be used to increase the accuracy of detecting heterozygous samples.

Allele specific hybridization can be used to detect sequence variants, including complete haplotypes of a subject (e.g., a mammal such as a human). See, Stoneking et al. (1991) *Am. J. Hum. Genet.* 48:370-382; and Prince et al. (2001) *Genome Res.* 11:152-162. In practice, samples of DNA or RNA from one or more subjects can be amplified using pairs of primers and the resulting amplification products (i.e., amplicons) can be immobilized on a substrate (e.g., in discrete regions). The amplicons can be detectably-labeled during the PCR amplification process (e.g., using one or more detectably labeled dNTPs) or subsequent to the amplification process using a variety of chemical or enzymatic techniques such as nick-translation. In some embodiments, one of the primers used in the amplification reaction is biotinylated (e.g., at the 5' end of reverse primer) and the resulting biotinylated amplification product is immobilized on an avidin or streptavidin coated substrate. Hybridization conditions are selected such that a nucleic acid probe can specifically bind to the sequence of interest, e.g., a nucleic acid containing the SNP. Such hybridizations typically are performed under high stringency. High stringency conditions can include the use of low ionic strength solutions and high temperatures for washing. For example, high stringency conditions can include hybridization at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. In some embodiments, the probes can be labeled (e.g., fluorescently) to facilitate detection. In some embodiments, the nucleic acid probes that can specifically bind to a corresponding amplicon are immobilized on a substrate in discrete regions, and contacted with detectably labeled amplicons. The binding of a detectably-labeled amplicon to a corresponding probe indicates the presence of the SNP so amplified in the biological sample. Suitable conditions and methods for detecting SNP using nucleic acid arrays are further described in, e.g., Lamy et al., *Nucleic Acids Research* 34(14): e100 (2006); European Patent Publication No. 1234058; U.S. Publication Nos. 20060008823 and 20030059813; and U.S. Pat. No. 6,410,231.

Allele-specific restriction digests can be performed in the following manner. For nucleotide sequence variants that introduce a restriction site, restriction digest with the particular restriction enzyme can differentiate the alleles. For sequence variants that do not alter a common restriction site, mutagenic primers can be designed that introduce a restriction site when the variant allele is present or when the wild type allele is present. A portion of a nucleic acid can be amplified using the mutagenic primer and a wild type primer, followed by digest with the appropriate restriction endonuclease. Alternatively, the restriction analysis can be done directly on unamplified genomic DNA from a subject.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluorescein and one primer labeled with a red dye such as sulforhodamine). Amplification products can be analyzed for green and red fluorescence in a plate reader. See, Myakishev et al. (2001) Genome 11:163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Any of the methods of detecting sequence variants can, optionally, be performed in formats that allow for rapid preparation, processing, and analysis of multiple samples.

In some embodiments, a biomarker can be a variant polypeptide (e.g., SLCO2B1 polypeptide containing a glutamine at position 312 in place of arginine, SLCO1B3 polypeptide containing an alanine at position 112 in place of serine, or SLCO1B3 polypeptide containing an isoleucine at position 233 in place of methionine). As used herein, the term "SLCO2B1 polypeptide" or "SLCO2B1 protein" refers to a chain of amino acids, regardless of post-translational modifications, that has ability to transport extracellular DHEAS into prostate cancer cells. The term "SLCO1B3 polypeptide" or "SLCO1B3 protein" refers to a chain of amino acids, regardless of post-translational modifications, that has ability to transport extracellular testosterone into cells. Antibodies having specific binding affinity for such variant polypeptides can be used to detect the presence of the biomarker. Variant polypeptides can be produced in various ways, including recombinantly, as known in the art. Host animals such as rabbits, chickens, mice, guinea pigs, and rats can be immunized by injection of a variant polypeptide. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Polyclonal antibodies are heterogeneous populations of antibody molecules that are contained in the sera of the immunized animals. Monoclonal antibodies, which are homogeneous populations of antibodies to a particular antigen, can be prepared using a variant polypeptide and standard hybridoma technology. In particular, monoclonal antibodies can be obtained by any technique that provides for the production of antibody molecules by continuous cell lines in culture such as described by Kohler et al. (1975) *Nature* 256:495, the human B-cell hybridoma technique (Kosbor et al. (1983) *Immunology Today* 4:72; Cote et al. (1983) *Proc. Natl. Acad. Sci USA* 80:2026), and the EBV-hybridoma technique (Cole et al., Monoclonal Antibodies and Cancer Therapy, Alan R. Liss, Inc., pp. 77-96 (1983). Such antibodies can be of any immunoglobulin class including IgG, IgM, IgE, IgA, IgD and any subclass thereof. A hybridoma producing monoclonal antibodies can be cultivated in vitro or in vivo.

Antibody fragments that have specific binding affinity for a variant polypeptide can be generated using known techniques. For example, such fragments include but are not limited to Fab, F(ab')2, Fv, and single chain Fv (scFv) fragments. F(ab')2 fragments can be produced by pepsin digestion of an antibody molecule, while Fab fragments can be generated by reducing the disulfide bridges of F(ab')2 fragments. Alternatively, Fab expression libraries can be constructed. See, for example, Huse et al. (1989) *Science* 246:1275. An scFv fragment is a single polypeptide chain that includes both the heavy and light chain variable regions of the antibody from which the scFv is derived. Once produced, antibodies or fragments thereof are tested for antigen recognition by standard immunoassay methods including ELISA techniques, radioimmunoassays and Western blotting. See, Short Protocols in Molecular Biology, Chapter 11, Green Publishing Associates and John Wiley & Sons, edited by Ausubel et al., 1992.

In one embodiment, a method described herein can include identifying the subject's SLCO2B1 genotype at two or three SNPs (e.g., rs12422149 and rs1789693; rs12422149 and rs1077858; rs1789693 and rs1077858; or rs12422149, rs1789693, and rs1077858) and classifying the subject as having a likelihood of responding for a longer duration of time or responding for a shorter duration of time depending on the SNP genotype. The subject's genotype can be identified by determining the nucleotide present at the desired SNP sites in a biological sample from a subject, as discussed above. The presence of two or three of rs12422149 (GG), rs1789693 (TT), and rs1077858 (AG/GG) is predictive that a subject is not likely to respond to ADT, ketoconazole, or abiraterone therapy for as long as a subject having the presence of three or more of rs12422149 (AA/AG), rs1077858 (AA), rs1789693 (AA), and rs1789693 (AT). As described herein, the rs12422149A>G (Gln312Arg), rs1789693A>T and rs1077858A>G variants in exon 7 (position 935 of cDNA), intron 7 and intron 8, respectively, of SLCO2B1 are associated with decreased time to progression (TTP) during ADT therapy and are referred to as risk alleles herein. A decreased TTP significantly affects the efficacy of ADT. Furthermore, there is an additive effect of the risk alleles across the three SLCO2B1 polymorphisms. That is, increasing the number of risk alleles (GG at rs12422149, TT at rs1789693, and AG/GG at rs1077858) further decreases TTP during ADT. For example, a subject having two or three of rs12422149 (GG), rs1789693 (TT), and rs1077858 (AG/GG) may have a duration of response that is at least 8 months, 9 months, 10 months, 11 months, 12 months, 13, months, 14 months, 15 months, 16 months, 17 months, 18 months, 19 months, 20 months, 21 months, 22 months, 23 months, or 24 months shorter than a subject with zero or one risk allele. For example, patients with two risk alleles had a 12-month shorter TTP compared with patients with zero or one risk allele. Patients with three risk alleles had an 18-month shorter TTP compared with patients with zero or one risk allele. See Table 4.

The methods described herein further can include identifying the subject's SLCO1B3 genotype at rs4149117 (334T>G; Ser112Ala) and/or rs7311358 (669G>A; Met233Ile). The SNPs at rs4149117 and rs7311358 are in complete linkage disequilibrium and exhibit different transport efficiencies. See Hamada et al,. 2008, supra. The rs4149117 T allele and rs7311358 G allele each are considered a risk allele. For example, the methods described herein can include detecting the nucleotide present at SLCO1B3 nucleotide SNP site rs4149117 and/or rs7311358. The presence of SLCO1B3 rs4149117 (GT/TT) and any one SLCO2B1 risk allele results in a further reduction in TTP during ADT compared with patients having any SLCO1B3 rs4149117 genotype and favorable SLCO2B1 alleles. The presence of SLCO1B3 rs7311358 (AG/GG) and any one SLCO2B1 risk allele also results in a further reduction in TTP during ADT compared with patients having any SLCO1B3 rs7311358 genotype and favorable SLCO2B1 alleles. Furthermore, the presence of rs4149117 (GT/TT) further enhances the additive effect of the presence of the three SLCO2B1 risk alleles.

The methods described herein can be carried out using a computer programmed to receive data (e.g., data from a chip containing a panel of SNPs, indicating whether a subject contains SNPs associated with response to ADT, ketoconazole, or abiraterone therapy). The computer can output for display information related to a subject's biomarkers, and the likelihood of the duration of time that the subject will be responsive to ADT, ketoconazole, or abiraterone therapy.

This document also provides methods and materials to assist medical or research professionals in determining the length of time whether or not a subject is likely to respond to or not respond to ADT, ketoconazole, or abiraterone therapy. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining whether a subject has one or more biomarkers associated with ADT, ketoconazole, or abiraterone therapy (e.g., the SNPs listed in Tables 4 and 5), and (2) communicating information about the biomarkers to that professional.

In some embodiments, a method for assessing the likelihood that ADT, ketoconazole, or abiraterone therapy will be effective in a subject can include receiving a biological sample obtained from the subject, assaying the sample to determine the number of SLCO2B1 risk alleles (e.g., by determining the particular genotype at rs12422149, rs1789693, and rs1077858), communicating to a medical professional information about whether the wild type or variant allele(s) are present in the sample, and, in some cases, before or after the first step, communicating to a medical professional information indicating that the presence of the variant allele(s) correlates with responsiveness to ADT, ketoconazole, or abiraterone therapy. In some embodiments, the sample also can be assayed to determine if SLCO1B3 risk alleles are present.

After information regarding a subject's biomarkers is reported, a professional can take one or more actions that can affect patient care. For example, a medical professional can record the information in a subject's medical record and/or in an electronic database. In some cases, a medical professional can record that the subject is likely or not likely to respond to ADT, ketoconazole, or abiraterone therapy, or otherwise transform the patient's medical record, to reflect the patient's medical condition. In some cases, a medical professional can review and evaluate a patient's medical record, and can assess multiple treatment strategies for clinical intervention of a patient's condition.

A professional (e.g., medical professional) can communicate information regarding biomarker analysis to a subject or a subject's family. In some cases, a professional can provide a subject and/or a subject's family with information regarding ADT, ketoconazole, or abiraterone therapy, including treatment options and potential side effects. In some cases, a professional can provide a copy of a subject's medical records to communicate information regarding biomarker analysis and/or disease states to a specialist.

A professional (e.g., research professional) can apply information regarding a subject's biomarkers to advance research into ADT, ketoconazole, or abiraterone therapy. For example, a researcher can compile data on the presence of particular biomarkers (e.g., SNPs) with information regarding the efficacy of ADT, ketoconazole, or abiraterone therapy, or side effects associated with ADT, ketoconazole, or abiraterone therapy. In some cases, a research professional can obtain a subject's biomarker information to evaluate the subject's enrollment, or continued participation in a research study or clinical trial. In some cases, a research professional can communicate a subject's biomarker information to a medical professional, or can refer a subject to a medical professional for clinical assessment and/or treatment.

Any appropriate method can be used to communicate information to another person (e.g., a professional), and information can be communicated directly or indirectly. For example, a laboratory technician can input biomarker information into a computer-based record. In some cases, information can be communicated by making a physical alteration to medical or research records. For example, a medical professional can make a permanent notation or flag a medical record for communicating information to other medical professionals reviewing the record. Any type of communication can be used (e.g., mail, e-mail, telephone, and face-to-face interactions). Information also can be communicated to a professional by making that information electronically available to the professional. For example, information can be placed on a computer database such that a medical professional can access the information. In addition, information can be communicated to a hospital, clinic, or research facility serving as an agent for the professional.

Altered Transporter Activity

In some embodiments, a nucleotide sequence variant can alter the activity of a polypeptide encoded by the SLCO2B1 gene. For example, a nucleotide sequence variant can result in increased or decreased activity of transporting extracellular DHEAS into prostate cancer cells. Activity of a SLCO2B1 polypeptide can be determined by, for example, measuring the level of SLCO2B1 activity in the subject using, for example, the in vitro methods described herein. See the DHEAS uptake assay described in Example 3.

In some embodiments, a nucleotide sequence variant can alter the activity of a polypeptide encoded by the SLCO1B3 gene. For example, a nucleotide sequence variant can result in increased or decreased activity of transporting testosterone into cells. Activity of a SLCO1B3 polypeptide can be determined by, for example, measuring the level of SLCO1B3 activity in the subject using, for example, an in vitro testosterone transport assay. In general, cellular uptake of testosterone can be measured by incubating labeled testosterone with prostate cancer cells transfected with a nucleic acid encoding the variant SLCO1B3 polypeptide then assessing the amount of labeled testosterone within the cells. See, for example, Hamada et al., 2008, supra.

Altered activity also can be evaluated by determining whether a SLCO2B1 or SLCO1B3 nucleic acid of a subject contains one or more sequence variants correlated with increased or decreased activity (e.g., DHEAS uptake by a SLCO2B1 polypeptide or testosterone uptake by a SLCO1B3 polypeptide). For example, a SLCO2B1 polypeptide having a glutamine substituted for arginine at position 312 has increased ability to transport extracellular DHEAS into prostate cancer cells. A SLCO1B3 polypeptide containing an alanine at position 112 in place of serine or an isoleucine at position 233 in place of methionine has decreased ability to transport extracellular testosterone into prostate cancer cells.

As used herein, the term "decreased activity" refers to a decrease (e.g., a 5%, 10%, 15%, 20%, 25%, 30%, 40%, 50%, 60%, 70%, 75%, 80%, 90%, 95%, or 100% decrease) in SLCO2B1 or SLCO1B3 activity of a subject, as compared to a control level of a corresponding activity. Similarly, the term "increased activity" refers to an increase (e.g., a 5%, 10%, 15%, 20%, 25%, 30%, 40%, 50%, 60%, 70%, 75%, 80%, 90%, 95%, 100%, or more than 100% increase) in SLCO2B1 or SLCO1B3 activity of a subject, as compared to a control level of a corresponding activity. A control level of SLCO2B1 activity can be, for example, an average level of SLCO2B1 activity in a population of individuals. Similarly, control levels of SLCO1B3 activity can be based on average level of SLCO1B3 activity in a population of individuals. In one embodiment, the population includes individuals that do not contain particular SLCO2B1 or SLCO1B3 nucleotide sequence variants or particular SLCO2B1 or SLCO1B3 amino acid sequence variants. Alternatively, a control level of DHEAS transporter activity can refer to the level of DHEAS transporter activity in a control subject (e.g., a subject that does not contain a SLCO2B1 nucleic acid containing a variant). A control level of testosterone transporter activity can refer to the level of testosterone transporter activity in a control subject (e.g., a subject that does not contain a SLCO1B3 nucleic acid containing a variant). Control subjects will generally be, but not necessarily, male subjects.

In some embodiments, evaluation of SLCO2B1 (or SLCO2B1 and SLCO1B3) activity can be used in diagnostic assays to predict the duration of time a particular therapy may be useful in a subject (e.g., a patient having prostate cancer), or to tailor particular treatment regimens to an individual. In patients having prostate cancer and increased SLCO2B1 activity, increased monitoring of the patient can be performed. As described herein, the rs12422149G>A polymorphism, which results in substitution of a glutamine for arginine at position 312 of the SLCO2B1 polypeptide, causes augmented DHEAS uptake, androgen receptor activation and increased cell proliferation in prostate cancer cells.

Articles of Manufacture

This document also provides articles of manufacture that can include, for example, materials and reagents that can be used to determine whether a subject has a biomarker for predicting response to ADT, ketoconazole, or abiraterone treatment. An article of manufacture can include, for example, nucleic acids and/or polypeptides immobilized on a substrate (e.g., in discrete regions, with different populations of isolated nucleic acids or polypeptides (e.g., SLCO2B1 polypeptides) immobilized in each discrete region) such as in a nucleic acid array. For example, a nucleic acid array can include populations of SLCO2B1 and SCLO1B3 nucleic acids immobilized on a substrate that hybridize to at least two SNPs described herein. In embodiments in which the substrate includes a plurality of discrete regions, different populations of isolated nucleic acids or polypeptides can be immobilized in each discrete region. Thus, each discrete region of the substrate can include a different SCLO2B1 or SCLO1B3 nucleic acid or SCLO2B1 polypeptide sequence variant. The nucleic acids can be DNA, RNA, modified DNA or RNA, or a hybrid, where the nucleic acid contains any combination of deoxyribo- and ribo-nucleotides, and any combination of uracil, adenine, thymine, cytosine and guanine, as well as other bases such as inosine, xanthine, and hypoxanthine. The nucleic acid arrays can be attached to a solid substrate, e.g., a porous or non-porous material that is insoluble. The nucleic acids can be immobilized on the substrate covalently or non-covalently.

Suitable substrates can be of any shape or form and can be constructed from a natural or synthetic material. The composition of the substrate to which the nucleic acids are attached (either 5' or 3' terminal attachment) generally depends on the method of attachment (e.g., covalent attachment). Non-limiting examples of substrates include plastics, resins, polysaccharides, silica or silica-based materials, functionalized glass, modified silicon, carbon, metals, inorganic glasses, membranes, nylon, natural fibers such as silk, wool and cotton, or polymers. The material from which the substrate is composed can have reactive groups such as carboxy, amino, or hydroxyl groups, which are used for attachment of the nucleic acids. Polymeric substrates can include, e.g., polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly)vinylidenefluoride, polycarbonate, or polymethylpentene (see, e.g., U.S. Pat. No. 5,427,779). Alternatively, the nucleic acids can be attached to the substrate without the use of such functional groups. In some embodiments, a substrate is glass, silicon, metal, plastic, cellulose, or a composite. In some embodiments, a suitable substrate can include a multiwell plate or membrane, a glass slide, a chip, or particles.

Many suitable particles are known in the art and include, e.g., particles such as Luminex®-type encoded particles, magnetic particles, and glass particles. Exemplary particles can have a variety of sizes and physical properties. Particles can be selected to have a variety of properties useful for particular experimental formats. For example, particles can be selected that remain suspended in a solution of desired viscosity or to readily precipitate in a solution of desired viscosity. Particles can be selected for ease of separation from sample constituents, for example, by including purification tags for separation with a suitable tag-binding material, paramagnetic properties for magnetic separation, and the like.

In some embodiments, encoded particles are used. Each particle includes a unique code (such as a bar code, luminescence code, fluorescence code, a nucleic acid code, and the like). Encoding can be used to provide particles for evaluating different nucleic acids in a single biological sample. The code is embedded (for example, within the interior of the particle) or otherwise attached to the particle in a manner that is stable through hybridization and analysis. The code can be provided by any detectable means, such as by holographic encoding, by a fluorescence property, color, shape, size, weight, light emission, quantum dot emission and the like to identify particle and thus the capture probes immobilized thereto. Encoding can also be the ratio of the levels of two or more dyes in one particle that is different than the ratio present in another particle. For example, the particles may be encoded using optical, chemical, physical, or electronic tags. Examples of such coding technologies are optical bar codes fluorescent dyes, or other means. In some embodiments, the particle code is a nucleic acid, e.g., a single stranded nucleic acid.

Different encoded particles can be used to detect or measure multiple nucleic acids (e.g., multiple SNP genotypes) in parallel, so long as the encoding can be used to identify the nucleic acid (corresponding to an analyte nucleic acid) on a particular particle, and hence the presence or amount of the analyte nucleic acid (e.g., a SNP genotype from a biological sample) being evaluated. A sample can be contacted with a plurality of such coded particles. When the particles are evaluated, e.g., using a fluorescent scanner, the particle code is read as is the fluorescence associated with the particle from any probe used to evaluate modification of the intact substrate associated with the particles.

One exemplary platform utilizes mixtures of fluorescent dyes impregnated into polymer particles as the means to identify each member of a particle set to which a specific capture probe has been immobilized. Another exemplary platform uses holographic barcodes to identify cylindrical glass particles. For example, Chandler et al. (U.S. Pat. No. 5,981,180) describes a particle-based system in which different particle types are encoded by mixtures of various proportions of two or more fluorescent dyes impregnated into polymer particles. Soini (U.S. Pat. No. 5,028,545) describes a particle-based multiplexed assay system that employs time-resolved fluorescence for particle identification. Fulwyler (U.S. Pat. No. 4,499,052) describes an exemplary method for using particle distinguished by color and/or size. U.S. Publication Nos. 2004-0179267, 2004-0132205, 2004-0130786, 2004-0130761, 2004-0126875, 2004-0125424, and 2004-0075907 describe exemplary particles encoded by holographic barcodes.

U.S. Pat. No. 6,916,661 describes polymeric microparticles that are associated with nanoparticles that have dyes that provide a code for the particles. The polymeric microparticles can have a diameter of less than one millimeter, e.g., a size ranging from about 0.1 to about 1,000 micrometers in diameter, e.g., 3-25 µm or about 6-12 µm. The nanoparticles can have, e.g., a diameter from about 1 nanometer (nm) to about 100,000 nm in diameter, e.g., about 10-1,000 nm or 200-500 nm.

Nucleic acids or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acids are typically about 20 nucleotides in length, but can vary from about 10 nucleotides to about 1000 nucleotides in length.

Each polynucleotide (of a plurality of polynucleotides) on an array can be immobilized at predetermined positions such that each polynucleotide can be identified by its position. Exemplary polynucleotide arrays for use in the methods and kits described herein are described in, e.g., U.S. Pat. Nos. 6,197,599; 5,902,723; and 5,871,928.

In some embodiments, an array of nucleic acids can have less than 100,000 (e.g., less than 90,000; less than 80,000; less than 70,000; less than 60,000; less than 50,000; less than 40,000; less than 30,000; less than 20,000; less than 15,000; less than 10,000; less than 5,000; less than 4,000; less than 3,000; less than 2,000; less than 1,500; less than 1,000; less than 750; less than 500, less than 200, less than 100, or less than 50) different nucleic acids.

In one embodiment, to detect a particular allele of a nucleic acid, for example, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al. (1996) *Nature Genet.* 14:441-447; and U.S. Pat. Nos. 5,770,722 and 5,733,729.

Also provided are kits containing any of the nucleic acid arrays described herein. The kits can optionally contain instructions for detecting one or more SLCO2B1 or SCLO1B3 SNP genotypes described herein (e.g., one or more SNP genotypes depicted in Tables 4 and 5). The kits can optionally include, e.g., a control biological sample or control labeled-amplicon set containing known amounts of one or more amplicons recognized by nucleic acid probes of the array.

In some embodiments, the kits can include one or more reagents for processing a biological sample. For example, a kit can include reagents for isolating genomic DNA from a biological sample and/or reagents for amplifying isolated genomic DNA (e.g., buffers, dNTPs, or polymerase). The kits also can optionally, contain one or more reagents for detectably-labeling genomic DNA or DNA amplicon (e.g., one or more detectably-labeled dNTPs).

In some embodiments, the kits can include a software package for analyzing the results of, e.g., a microarray analysis or expression profile.

A kit also can include an antibody for detecting the expression of a variant SLCO2B1 and/or SLCO1B3 polypeptide and optionally, instructions for detecting the variant polypeptide and/or a detection antibody that includes a detectably-labeled antibody capable of binding to the antibody having binding affinity for the variant polypeptide.

The kits described herein also can optionally include instructions for treating a prostate cancer patient based on the presence or absence of one or more risk alleles described herein.

The invention is further described in the following examples, which do not limit the scope of the invention described in the claims.

EXAMPLES

Example 1

Patient Selection and Database

An androgen deprivation therapy (ADT) cohort was generated from the Prostate Clinical Research Information System (CRIS) at Dana-Farber Cancer Institute (DFCI; Boston, Mass.). The CRIS system consists of data-entry software, a central data repository, collection of patient data including comprehensive follow-up of all patients, and tightly integrated security measures as described in Oh et al., *Clin Genitourin Cancer* 5:61-66 (2006). All patients provided written informed consent to allow the collection of tissue and blood and the analysis of clinical and genetic data for research purposes. The original ADT cohort of 595 CaP patients who were treated with ADT (orchiectomy or luteinizing hormone-releasing hormone agonist, with or without an antiandrogen) was originally assembled for the study of predictive factors for the efficacy of ADT in men with HSPC either with or without metastases as described in Ross et al., *Cancer* 112:1247-53 (2008), and Ross et al., *J Clin Oncol.* 26:842-847 (2008). In the present study, patients without PSA data after ADT initiation and patients whose DNA was not of adequate quality to allow genotyping in more than 50% of genotyping assays were excluded from analyses, resulting in the final cohort size of 538 patients. The clinical data and outcomes collection were as previously described in Ross et al., *Cancer* 112:1247-53 (2008), and Ross et al., *J Clin Oncol.* 26:842-847 (2008). Data were collected on patient and disease baseline clinical characteristics, ADT treatment, and treatment outcome. Medical records were reviewed on 9% of the cohort for quality control purposes and found to be of high quality.

The efficacy of ADT was evaluated using prostate-specific antigen (PSA) time to progression (TTP), defined as the duration of time from ADT initiation to the date of PSA progression. PSA progression was defined as two rises in PSA (at least 1 week apart) greater than a nadir value while receiving ADT. The first rise needed to be greater than the nadir PSA plus 0.02 ng/ml and the second rise needed to be greater than the nadir and also greater than the first rise. Initiation of secondary hormone therapy for rising PSA before fulfillment of the definition of progression also was considered as a progression event, with the date of starting the secondary hormone therapy as the progression date. TTP during ADT was defined as the duration of time from ADT initiation to the date of ADT progression or the date of initiation of secondary hormonal therapy, or was censored among patients who did not progress at the date last known progression free or the date of death who died without progression.

The clinical characteristics of this ADT study cohort are presented in Table 1. In Table 1, T refers to clinical stage, M refers to yes or no metastases, RP refers to radical prostatectomy, and RT refers to radiation therapy. A Gleason score of 6 or less is mildly aggressive, 7 is moderately aggressive, and 8 or more is highly aggressive. With a median follow-up of 5.1 years after ADT initiation (ranging from 1 month to 17 years), 393 patients had progressed and 145 had not. Median TTP during ADT was 22.7 months [95% confidence interval (CI), 19.0, 26.1 months].

TABLE 1

Characteristics of the Cohort (n = 538)

|  | N | % |
|---|---|---|
| Clinical T stage at Diagnosis | | |
| T1 | 130 | 24.2 |
| T2 | 153 | 28.4 |
| T3-4 | 25 | 4.6 |
| Tx | 230 | 42.7 |
| Clinical M stage at Diagnosis | | |
| M0 | 202 | 37.5 |
| M1 | 81 | 15.1 |
| Mx | 255 | 47.4 |
| Clinical N stage at Diagnosis | | |
| N0 | 182 | 33.8 |
| N1 | 37 | 6.9 |
| Nx | 319 | 59.3 |
| Biopsy Gleason at Diagnosis | | |
| 6 or less | 96 | 17.8 |
| 7 | 164 | 30.5 |
| 8 or more | 185 | 34.4 |
| Unknown | 93 | 17.3 |
| Definitive local therapy | | |
| RP +/− RT | 208 | 38.7 |
| RT only/other | 166 | 30.9 |
| None | 164 | 30.5 |
| Hormonal Rx for local disease | | |
| No | 451 | 83.8 |
| Yes | | 16.2 |
| Metastases at ADT initiation | | |
| No | 273 | 50.7 |
| Yes | 265 | 49.3 |
| Type of ADT | | |
| LHRH analog | 489 | 90.9 |
| Orchiectomy | 37 | 6.9 |
| Orchiectomy + LHRH analog | 12 | 2.2 |
| Receive Anti-androgen during ADT | | |
| No | 181 | 33.6 |
| Yes | 357 | 66.4 |

|  | Median | Range |
|---|---|---|
| Age at diagnosis, years (n = 519) | 62 | 42-84 |
| PSA at diagnosis, ng/ml (n = 450) | 14.95 | 0.90-6849 |
| PSA at ADT initiation, ng/ml (n = 395) | 16.40 | 0-15090 |
| Years from diagnosis to ADT initiation (n = 519) | 2.23 | 0-19 |

Example 2

Association of SLCO2B1 SNPs with TTP During ADT

The human SLCO2B1 gene, which is located on chromosome 11q13.4, contains 14 exons and 13 introns and encodes 709 amino acids. Haplotype-tagging SNPs (htSNP) from the SLCO2B1 gene locus (from ~2 kb region upstream of the gene to ~2 kb region downstream of the gene; ~59 kb in total) were chosen from genotyped SNPs in a Caucasian population (CEU) in the HapMap Project [Rel 21/phaseII Jan07, on National Center for Biotechnology Information B35 assembly, dbSNP b125, minor allele frequency (MAF) of $\geq 0.05$] with the program Tagger on a pairwise mode ($r^2 \geq 0.8$) (see de Bakker et al. *Nat Genet.* 38:1298-1303 (2006)). All nonsynonymous SNPs with a MAF greater than 0.05 or reported in the literature also were included. In total, 23 htSNPs of SLCO2B1 and two SLCO1B3 functional SNPs were selected for genotyping (Hamada et al., *Clin Cancer Res.* 14,3312-3318 (2008)). Five SNPs with a MAF of less than 5% were excluded from analysis. Thus, a total of 18 SNPs in SLCO2B1 and 2 SNPs in SLCO1B3 were included in the final statistical analysis. See Tables 2 and 3.

Genomic DNA was prepared from patients' peripheral blood samples using QIAamp DNA Blood mini kit (QIAGEN Inc, Valencia, Calif.). Genotyping was performed on the genomic DNA at the Molecular Genetics Core Facility at Children's Hospital Boston, Harvard Medical School using Sequenom iPLEX matrix-assisted laser desorption/ionization (MALDI)-time of flight mass spectrometry technology (Carlsbad, Calif.). Assays were designed using Sequenom's MassARRAY AssignDesigner application, version 3.0. Polymerase chain reaction (PCR) and single base extension (SBE) oligonucleotides were synthesized by Integrated DNA Technologies (Coralville, Iowa).

TABLE 2

Location and Position of SLCO2B1 htSNPs

| dbSNP-ID | Location in the SLCO2B1 locus | Position* |
|---|---|---|
| rs4944073 | Intron 1 | 7454340 |
| rs2712818 | Intron 1 | 74543497 |
| rs11236357 | Intron 1 | 74545253 |
| rs2851074 | Intron 1 | 74548067 |
| rs2851075 | Intron 1 | 74549016 |
| rs3819192 | Intron 3 | 74553149 |
| rs1789694 | Intron 6 | 74559330 |
| rs12422149 | Exon 7 | 74561225 |
| rs7947726 | Intron 7 | 74563722 |
| rs1676881 | Intron 7 | 74564506 |
| rs1789693 | Intron 7 | 74564813 |
| rs7117473 | Intron 7 | 74565201 |
| rs1676882 | Intron 7 | 74565910 |
| rs1077858 | Intron 8 | 74579249 |
| rs7118873 | Intron 8 | 74580510 |
| rs1676885 | Intron 9 | 74582926 |
| rs7116044 | Intron 11 | 74589602 |
| rs7951787 | 3'-flanking region | 74596186 |

*Positions are from NCBI Build 35.

TABLE 3

Genotyped SNPs and Their Association with TTP on ADT

| Gene | SNP | SNP genotype | N (%) | Median TTP (months) | HR* (95%CI) | P-Value** |
|---|---|---|---|---|---|---|
| SLCO2B1 | rs4944073 | cc | 332(63) | 21.8 | 1.00(reference) | 0.932 |
|  |  | cc/tt | 191(37) | 25.9 | 1.01(0.82,1.24) |  |

TABLE 3-continued

Genotyped SNPs and Their Association with TTP on ADT

| Gene | SNP | SNP genotype | N (%) | Median TTP (months) | HR* (95%CI) | P-Value** |
|---|---|---|---|---|---|---|
| SLCO2B1 | rs2712818 | gg | 64(13) | 22.5 | 1.00(reference) | 0.408 |
| | | gt | 244(51) | 20.5 | 1.10(0.79,1.53) | |
| | | tt | 173(36) | 25.0 | 0.94(0.67,1.33) | |
| SLCO2B1 | rs11236357 | aa/at | 209(42) | 25.9 | 1.00(reference) | 0.517 |
| | | tt | 284(58) | 21.6 | 1.07(0.87,1.32) | |
| SLCO2B1 | rs2851074 | cc | 301(61) | 25.7 | 1.00(reference) | 0.106 |
| | | ct/tt | 190(39) | 19.2 | 1.19(0.96,1.47) | |
| SLCO2B1 | rs2851075 | aa | 150(30) | 24.0 | 1.00(reference) | 0.375 |
| | | ag | 239(48) | 25.5 | 0.97(0.76,1.23) | |
| | | gg | 104(21) | 18.1 | 1.17(0.87,1.57) | |
| SLCO2B1 | rs3819192 | aa/ag | 67(14) | 25.0 | 1.00(reference) | 0.912 |
| | | gg | 423(86) | 22.5 | 0.98(0.73,1.33) | |
| SLCO2B1 | rs1789694 | cc/ct | 233(44) | 19.0 | 1.00(reference) | 0.093 |
| | | tt | 298(56) | 25.9 | 0.84(0.69,1.03) | |
| SLCO2B1 | rs12422149 | aa/ag | 98(18) | 31.5 | 1.00(reference) | 0.029 |
| | | gg | 434(82) | 20.9 | 1.40(1.06,1.84) | |
| SLCO2B1 | rs7947726 | aa/ag | 129(26) | 22.7 | 1.00(reference) | 0.092 |
| | | gg | 361(74) | 23.6 | 0.82(0.65,1.03) | |
| SLCO2B1 | rs1676881 | aa | 69(14) | 19.2 | 1.00(reference) | 0.245 |
| | | ag | 224(46) | 23.4 | 0.83(0.61,1.13) | |
| | | gg | 197(40) | 25.0 | 0.76(0.56,1.05) | |
| SLCO2B1 | rs1789693 | aa | 215(41) | 21.5 | 1.00(reference) | 0.007 |
| | | at | 228(43) | 26.3 | 1.07(0.86,1.34) | |
| | | tt | 82(16) | 14.5 | 1.60(1.19,2.16) | |
| SLCO2B1 | rs7117473 | aa | 395(82) | 23.4 | 1.00(reference) | 0.912 |
| | | ag/gg | 87(18) | 19.3 | 1.02(0.77,1.34) | |
| SLCO2B1 | rs1676882 | cc | 140(29) | 25.9 | 1.00(reference) | 0.641 |
| | | ct | 237(50) | 24.6 | 1.07(0.84,1.37) | |
| | | tt | 101(21) | 20.0 | 1.15(0.86,1.55) | |
| SLCO2B1 | rs1077858 | aa | 188(38) | 28.1 | 1.00(reference) | 0.009 |
| | | ag | 231(47) | 19.3 | 1.25(1.00,1.58) | |
| | | gg | 73(15) | 16.4 | 1.59(1.17, 2.17) | |
| SLCO2B1 | rs7118873 | gg/gt | 135(28) | 25.5 | 1.00(reference) | 0.069 |
| | | tt | 348(72) | 21.6 | 1.25(0.98,1.59) | |
| SLCO2B1 | rs1676885 | aa | 245(50) | 22.7 | 1.00(reference) | |
| | | ag | 213(43) | 20.9 | 0.90(0.72,1.11) | 0.090 |
| | | gg | 34(7) | 36.9 | 0.63(0.42,0.97) | |
| SLCO2B1 | rs7116044 | ac | 53(11) | 21.1 | 1.00(reference) | 0.655 |
| | | cc | 424(89) | 23.4 | 1.08(0.77,1.52) | |
| SLCO2B1 | rs7951787 | aa | 483(91) | 22.0 | 1.00(reference) | 0.492 |
| | | ag/gg | 47(9) | 24.7 | 1.13(0.80,1.61) | |
| SLCO2B3 | rs7311358 | aa | 372(69) | 23.5 | 1.00(reference) | 0.810 |
| | | ag/gg | 166(31) | 20.2 | 0.98(0.78,1.22) | |
| SLCO2B3 | rs4149117 | gg | 368(69) | 23.5 | 1.00(reference) | 0.719 |
| | | gt/tt | 162(31) | 20.2 | 1.01(0.80,1.26) | |

For statistical analysis, each SNP in the SLCO2B1 and SLCO1B3 genes was treated as a categorical variable with a common homozygote, a rare homozygote, and a heterozygote. A rare homozygote was combined with a heterozygote if the frequency of the rare homozygote was below 0.05 (for 12 SNPs). The median TTP were estimated using the Kaplan-Meier method, with 95% CIs for the median. To test the association between individual SNPs and TTP, the log-rank test was used. For SNPs with P values <0.05 from log-rank test, multivariable Cox regression models also were performed to adjust for clinical variables and their associations with TTP and for the interaction between SLCO2B1 and SLCO1B3. The statistical analysis was performed using SAS version 9.2 (SAS Institute, Cary, N.C.). All P values are two sided.

Three polymorphisms of SLCO2B1, rs12422149A>G (Arg312Gln) in exon 7, rs1789693A>T in intron 7 and rs1077858A>G in intron 8, were significantly associated with TTP during ADT in univariate analysis (P=0.029, 0.007 and 0.009, respectively) (Table 4 and FIGS. 1A, B, C). The differences in median TTP during ADT for the genotypes of these 3 SNPs were approximately 10 months (rs12422149), 7 months (rs1789693), and 12 months (rs1077858). In multivariate analysis adjusting for various clinical factors associated with TTP, the association between each of the three SNPs and TTP during ADT remained significant (P≤0.05, Table 4). The adjusted hazard ratios (HRs) and 95% CIs for progression on ADT were 1.40 (1.06, 1.84), 1.46 (1.07, 1.98) and 1.57 (1.15, 2.14) (Table 4).

cacy of ADT. It was hypothesized that different variants of the SLCO2B1 gene may transport external androgens or androgen conjugates into CaP cells at different efficiencies, resulting in varying responses to ADT.

Example 3

Differential DHEAS Uptake of SLCO2B1 Variants

To address the biological function of different SLCO2B1 variants in response to ADT, it was investigated whether the SLCO2B1 rs12422149A>G (Arg312Gln) SNP can influence the efficiency of DHEAS transport, thus affecting the intracellular level of androgen and the cellular response to ADT. The LNCaP CaP cell line was used for the kinetic analysis of DHEAS uptake with different SLCO2B1 variants

TABLE 4

SLCO2B1 Genotype Distribution and Its Association with TTP on ADT

| Gene | Genotype | N | Median TTP (months) | Univariate model HR (95% CI) | P-value | Multivariate model* HR (95% CI) | P-value |
|---|---|---|---|---|---|---|---|
| SLCO2B1 | rs12422149 | | | | | | |
| | AA/AG | 8 | 31.5 | 1.00 (reference) | 0.029 | 1.00 (reference) | 0.018 |
| | GG | 34 | 20.9 | 1.35 (1.03 1 77) | | 1.40 (1.06,1 84) | |
| SLCO2B1 | rs1789693 | | | | | | |
| | AA | 15 | 21.5 | 1.00 (reference) | 0.007 | 1.00 (reference) | 0.051 |
| | AT | 28 | 26.3 | 1.07 (0.86,1.34) | | 1.08 (0.86,1.34) | (0.018** |
| | TT | 2 | 14.5 | 1.60 (1.19 2 16) | | 1.46 (1.07 1 98) | |
| SLCO2B1 | rs1077858 | | | | | | |
| | AA | 88 | 28.1 | 1.00 (reference) | 0.009 | 1.00 (reference) | 0.008 |
| | AG | 31 | 19.3 | 1.25 (1.00,1.58) | | 1.33 (1.05,1.68) | |
| | GG | 3 | 16.4 | 1.59 (1.17,2.17) | | 1.57 (1.15,2.14) | |
| SLCO2B1 | No of risk genotype | | | | | | |
| | ≤1 | 35 | 30.9 | 1.00 (reference) | <0.0001 | 1.00 (reference) | <0.0001 |
| | 2 | 04 | 19.0 | 1.44 (1.15,1.80) | | 1.56 (1.24, 1.97) | |
| | 3 | 0 | 12.8 | 2.01 (1.42,2.85) | | 1.91 (1.34, 2.71) | |
| SLCO1B3 | rs4149117 | | | | | | |
| | GG | 68 | 23.5 | 1.00 (reference) | 0.717 | 1.00 (reference) | 0.719 |
| | GT/TT | 2 | 20.2 | 1.04 (0.84,1.29) | | 1.01 (0.80,1.26) | |
| SLCO1B3 | rs7311358 | | | | | | |
| | AA | 72 | 23.5 | 1.00 (reference) | 0.809 | 1.00 (reference) | 0.810 |
| | AG/GG | 66 | 20.2 | 1.03 (0.83,1.27) | | 0.98 (0.78, 1.22) | |

Figure 1D:
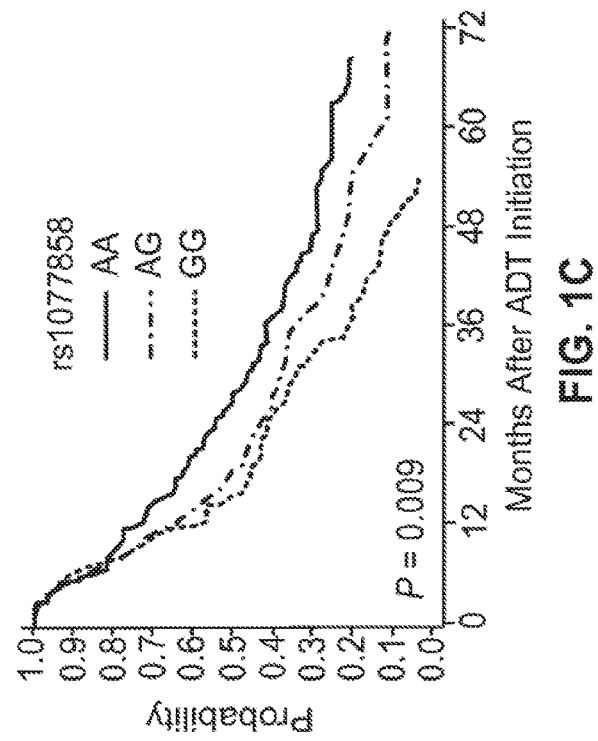

Minimal linkage disequilibrium was observed among the three SNPs, with pairwise correlation ($r^2$) ranging from 0.11 to 0.21. There was an additive effect of the alleles across the three SLCO2B1 polymorphisms. The population was stratified by the number of risk alleles that an individual carried. In this analysis, a risk allele was defined as the allele with a shorter TTP during ADT (GG at rs12422149, TT at rs1789693, and AG/GG at rs1077858). Increasing the number of risk alleles reduced the TTP during ADT (P<0.0001). Approximately an 18-month difference in median TTP was observed between patients with three of the risk alleles and those with zero or one risk allele (Table 4 and FIG. 1D). Individuals with two risk alleles showed a 12-month shorter TTP compared with those with zero or one risk allele (Table 4 and FIG. 1D). No significant association was detected between the genotypes of SLCO2B1 and patient clinical characteristics.

In short, the data in this example demonstrated that genetic variations in SLCO2B1 significantly affect the effibecause LNCaP has a low level of SLCO2B1 expression among all tested CaP cell lines.

Two full-length SLCO2B1 cDNAs, SLCO2B1-312Gln (having a G at the position 935) and SLCO2B1-312Arg (having an A at position 935), were cloned into the pCMV6-XL4 vector (OriGene Technologies, Rockville, Md.). The SLCO2B1 935G>A nucleotide exchange was introduced into the cDNA using the QuikChange Site-Directed Mutagenesis kit (Stratagene, La Jolla, Calif.). Primers used for the mutagenesis were 5'-TGAGCTTCAGTTTCGGCAAA-AGGTCTTAGCAGTCA-3' (SEQ ID NO:1) and 5'-TGACTGCTAAGACCTTTTGCCGAAACTGAAG-CTCA-3' (SEQ ID NO:2) (underlined sequences encode 312Arg). The correct construction of pCMV-SLCO-312Arg was confirmed by restriction enzyme site analysis and nucleotide sequence analyses.

LNCaP cells were maintained in RPMI 1640 supplemented with 10% fetal bovine serum (FBS). Twenty-four hours before transfection, $2 \times 10^5$ cells were seeded in 12-well plates using Phenol-Red free RPMI 1640 supplemented with 10% charcoal-stripped FBS. LNCaP cells were transiently transfected with pCMV-SLCO2B1-312Gln, pCMV-SLCO2B1-312Arg, or pCMV6-XL4 empty vector using Lipofectamine$^{2000}$ according to the manufacturer's instructions. Forty-eight hours post-transfection, cells were either harvested for RNA isolation or treated with DHEAS (Sigma-Aldrich, St. Louis, Mo.) for the DHEAS uptake assay.

Total RNA was isolated from cells using TRIzol reagent (Invitrogen, Carlsbad, Calif.) and then converted to cDNA using High Capacity cDNA Reverse Transcription kit (Applied Biosystems, Foster City, Calif.). The expression levels of SLCO2B1 and GAPDH were measured using a standard TaqMan PCR kit protocol. Experiments were carried out in triplicate for each data point. Real-time PCR primers and probe sets were inventoried products of Applied Biosystem (Assay ID: Hs00200670_m1and Hs02758991_g1).

All DHEAS uptake studies were performed using an incubation buffer containing 116 mM NaCl, 5.3 mM KCl, 1 mM $KH_2PO_4$, 0.8 mM $MgSO_4$, 5.5 mM D-glucose, and 20 mM HEPES, pH 7.4 at 37° C. Briefly, at 48 h after transfection, cells were harvested, washed three times using the incubation buffer, and then treated with different concentrations of DHEAS. At the defined time points, DHEAS uptake was stopped by washing the cells with the incubation buffer three times and the cells were dissolved in 100 µl 1% Triton X-100 solution in 1× phosphate buffered saline (PBS). The levels of DHEAS in cells were measured using the DHEAS ELISA kit (BioVendor, Candler, N.C.). The enzyme immunoassay test is based on the competition that occurs between an unlabeled antigen (present in standards, control and samples) and an enzyme-labeled antigen (conjugate) for a limited number of antibody binding sites on the microwell plate. The sensitivity of the kit is 5 ng/ml. The DHEAS ELISA tests were performed according to the manufacturer's instructions. Twenty-five µl of each of the samples, standards, or controls were used for each reaction. Samples were tested in triplicate. DHEAS concentrations were determined by comparing the absorbance values of samples with those obtained for the reference standards plotted on a standard curve. Cellular protein content was determined by using the BCA Protein Assay Reagent (Thermo Fisher Scientific, Rockford, Ill.) with bovine serum albumin as the standard. The levels of DHEAS in cells are represented as means±S.D. Graphs were prepared using GraphPad Prism 5.0 (GraphPad Software, San Diego, Calif.). Kinetic parameters (Km and Vmax) for DHEAS uptake activities of different SLCO2B1 variants were estimated by nonlinear regression using GraphPad Prism 5.0. Student's t test was performed to determine the statistical significance.

Figure 2A:
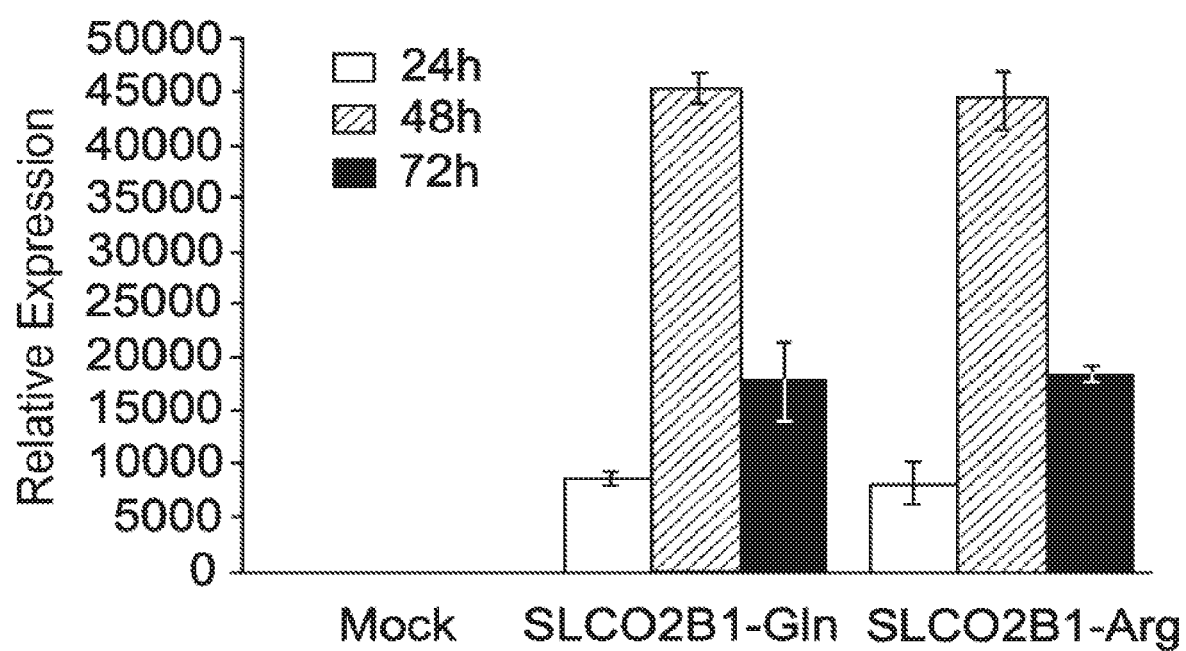
FIG. 2A-2C depict DHEAS (sulfated dehydroepiandrosterone) uptake by SLCO2B1 variants.
Figure 2B:
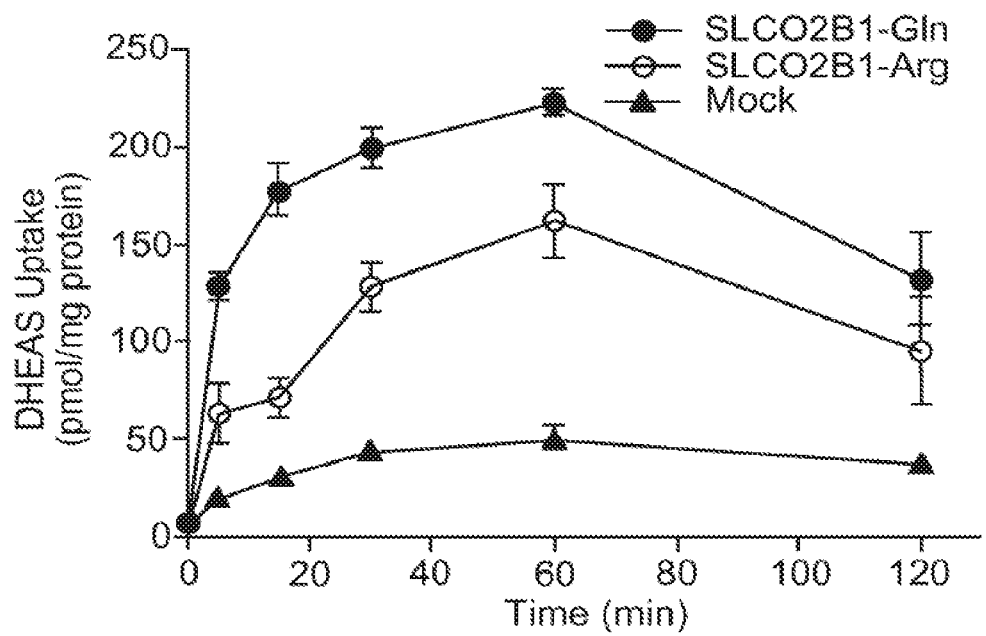

Both SLCO2B1-312Gln and SLCO2B1-312Arg were expressed at similar levels in transfected cells and their highest expression level was observed at 48 hours after transfection (FIG. 2A). FIG. 2B shows the time dependent uptake of DHEAS in various transfected cells. Upon incubation with 100 µM DHEAS, DHEAS uptake increased with increasing incubation time, and reached maximum levels at 1 hour. Compared with the mock-transfected LNCaP cells, cells over-expressing SLCO2B1-312Gln or -312Arg exhibited significantly higher levels of DHEAS uptake. Cells expressing the SLCO2B1-312Gln variant exhibited a maximal uptake of 223.38±8.55 pmol/mg protein, cells expressing the SLCO2B1-312Arg variant exhibited a maximal uptake of 162.76±25.73 pmol/mg protein, and the pCMV6-XL4 vector (mock) transfected cells exhibited uptake of 51.66±7.44 pmol/mg protein.

Figure 2C:
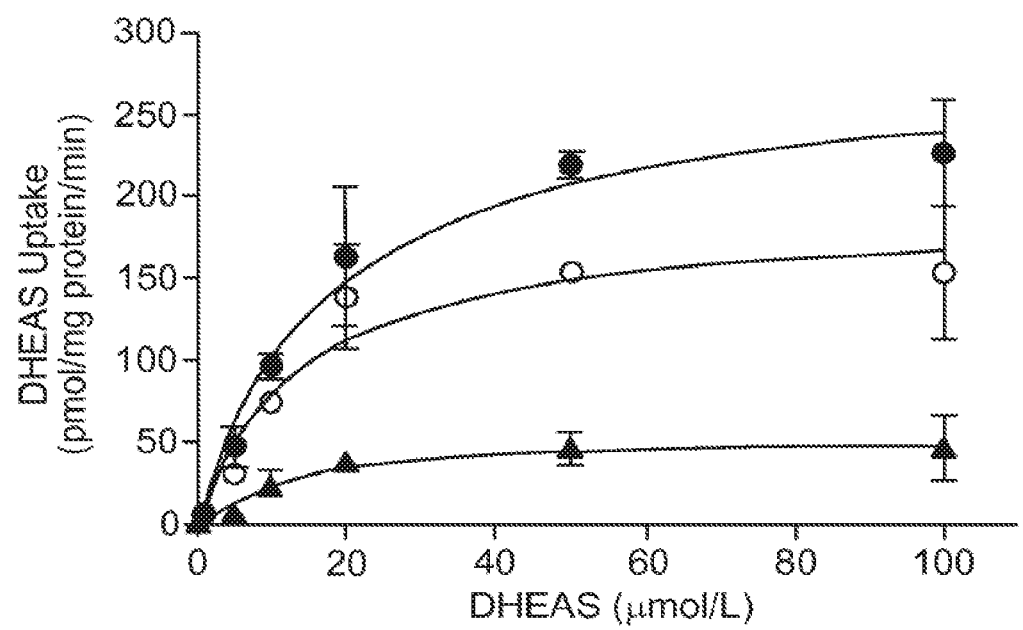

Further analysis of the kinetics of different SLCO2B1 variants mediating DHEAS uptake in different DHEAS concentrations demonstrated that increasing the concentration of DHEAS increased the uptake of DHEAS, and saturation can be reached at 60-100 µM (FIG. 2C). The best-fit $K_m$ values for the SLCO2B1-312Gln and SLCO2B1-312Arg variants were 17.65 µmol/L (95% CI, 9.303, 25.99 µmol/L) and 13.68 µmol/L (95% CI, 4.174, 23.20 µmol/L), respectively. The $V_{max}$ values for the 312Gln and 312Arg variants were 281.4 pmol/mg protein/min (95% CI, 236.1, 326.7 pmol/mg protein/min) and 189.5 pmol/mg protein/min (95% CI, 147.8, 231.2 pmol/mg protein/min), respectively. These results indicate that both SLCO2B1 variants can efficiently import DHEAS, though the SLCO2B1-312Gln allele exhibited a significantly greater efficiency. It was hypothesized that the higher efficiency of the SLCO2B1-312Gln variant in transporting extracellular DHEAS into CaP cells led to a greater ability to activate AR which, may, in turn, sustain cell growth, thereby explaining why patients with the SLCO2B1-312Gln variant exhibited a shorter TTP during ADT.

Example 4

The Impact of DHEAS Import on AR Signaling and Growth in CaP Culture Cells

To determine the biological influence of DHEAS uptake in AR activation, AR mediated PSA expression was compared in wild type LNCaP and LAPC-4 cells (another CaP cell line, maintained as described above for LNCaP cells) and cells that express different SLCO2B1 variants. The expression levels of AR and PSA were measured using a standard TaqMan PCR kit protocol (Hs02576345_m1 and Hs00171172_m1) as described in Example 3.

Figure 3A:
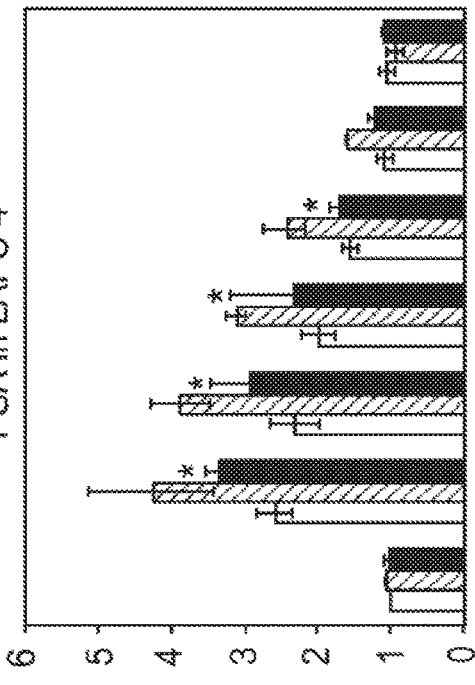
FIGS. 3A-3F depict the impact of SLCO2B1 variants on the AR mediated expression and cell growth.
Figure 3B:
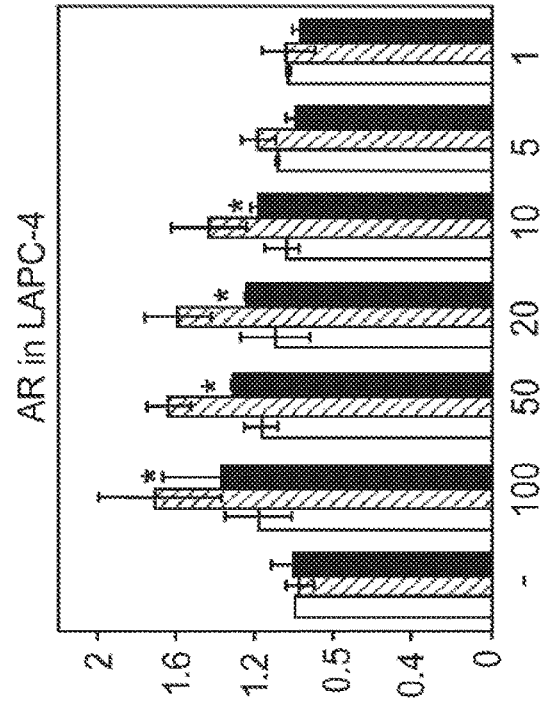
Figure 3C:
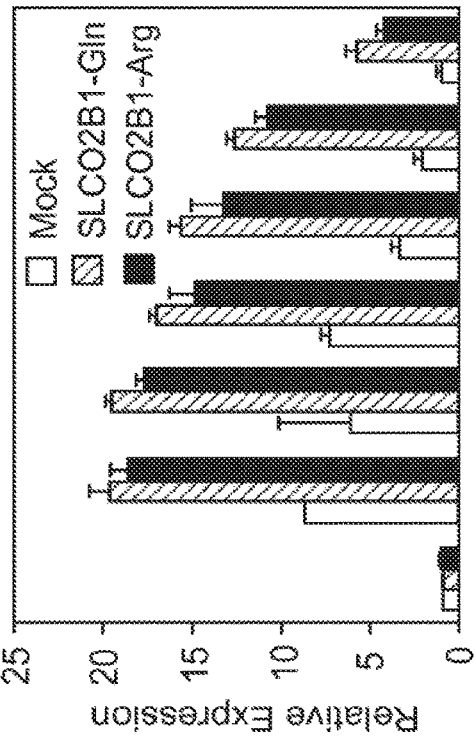
Figure 3D:
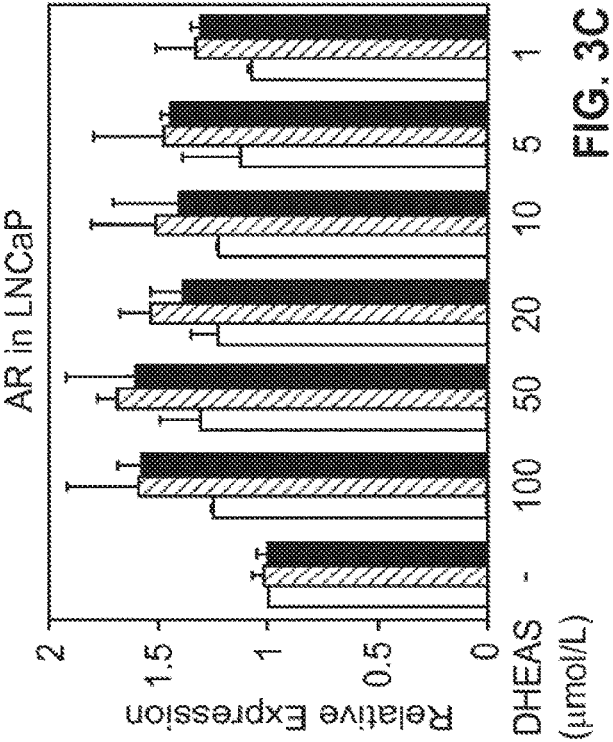

Increasing the DHEAS level up-regulated PSA expression in both wild type cell lines and cells transfected with SLCO2B1 (FIGS. 3A, B). While both LNCaP and LAPC-4 cell lines transfected with the SLCO2B1-Gln variant showed consistently higher PSA expression levels than those of cells transfected with the SLCO2B1-Arg variant (FIGS. 3A, B); this correlation was only statistically significant in LAPC-4 cells (FIG. 3B). Specifically, treatment with 100 µM DHEAS up-regulated the PSA expression in LAPC-4 cells harboring the SLCO2B1-Gln variant by 1.48-fold, compared to that in cells with the SLCO2B1-Arg variant. Interestingly, exposure to DHEAS also increased AR mRNA levels in both LNCaP and LAPC4 cell lines (FIGS. 3C, D). Specifically, cells carrying the SLCO2B1-Gln variant and treated with 100 µM DHEAS exhibited a 1.24-fold higher level of AR expression than that in cells with the SLCO2B1-Arg variant. Thus, up-regulation of PSA expression upon the treatment with DHEAS could be, in part, due to the increased levels of intracellular androgen and partly due to the increased expression of AR.

To corroborate the hypothesis that increasing the intracellular androgen level is involved in the development of the CRPC cells, the impact of DHEAS uptake on cell growth was determined. Cell proliferation was determined using a WST-1 kit (Roche, Indianapolis, Ind.). Briefly, cells were cultured in 96-well plates in androgen-depleted medium and were transfected with different alleles of SLCO2B1 expression plasmids before adding 100 µM DHEAS. Tetrazolium salt cell proliferation assay then was carried out at different days after transfection, following the manufacturer's instructions.

Figure 3E:
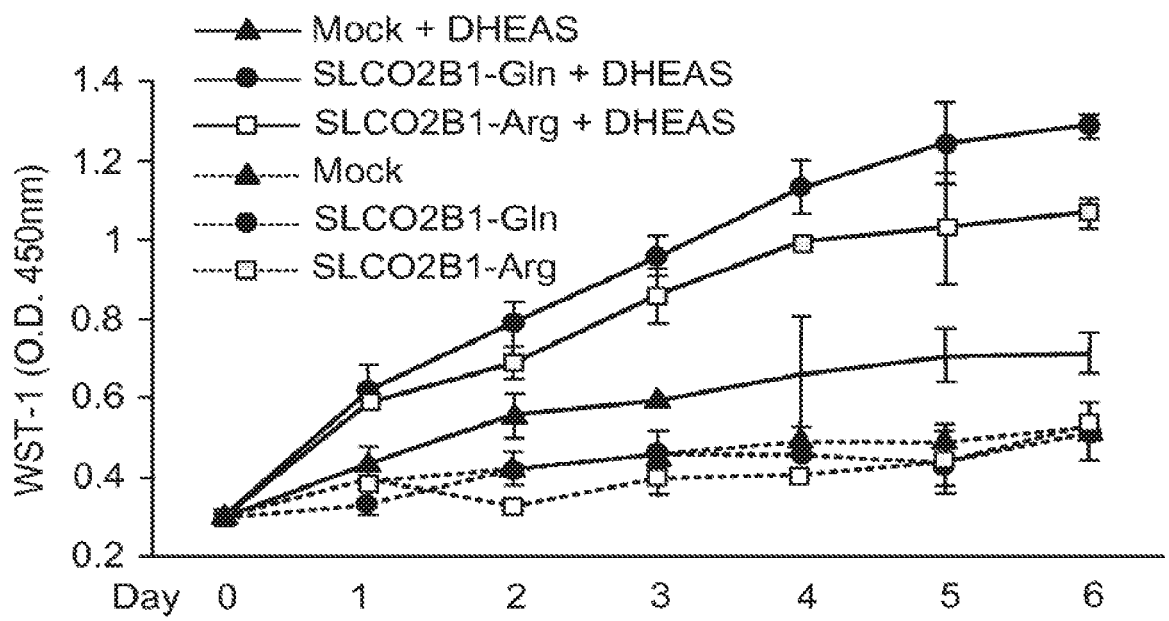
Figure 3F:
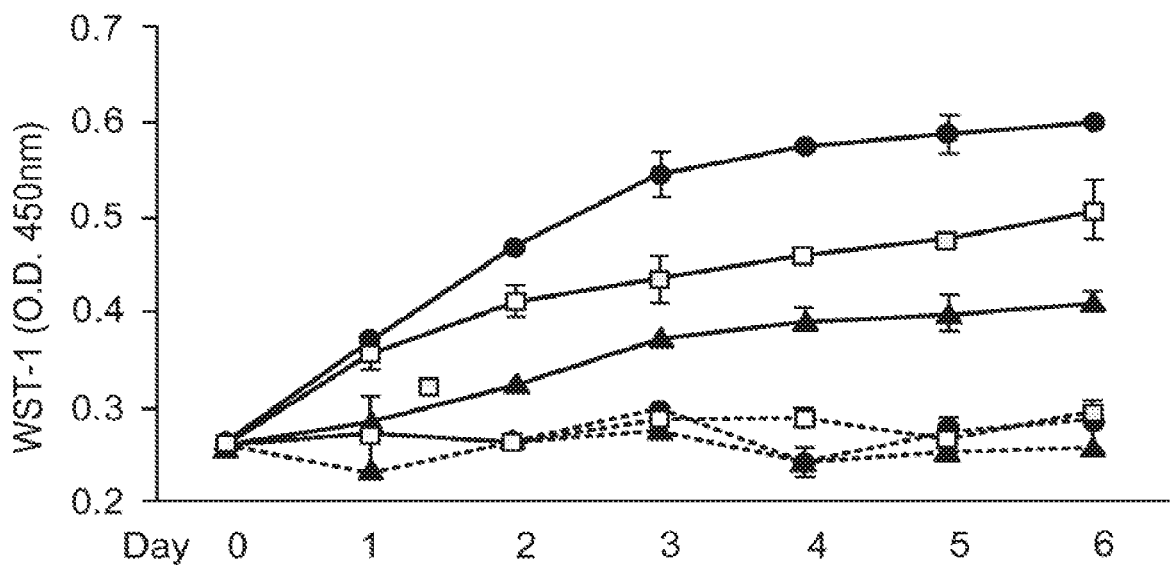
Figure 4A:
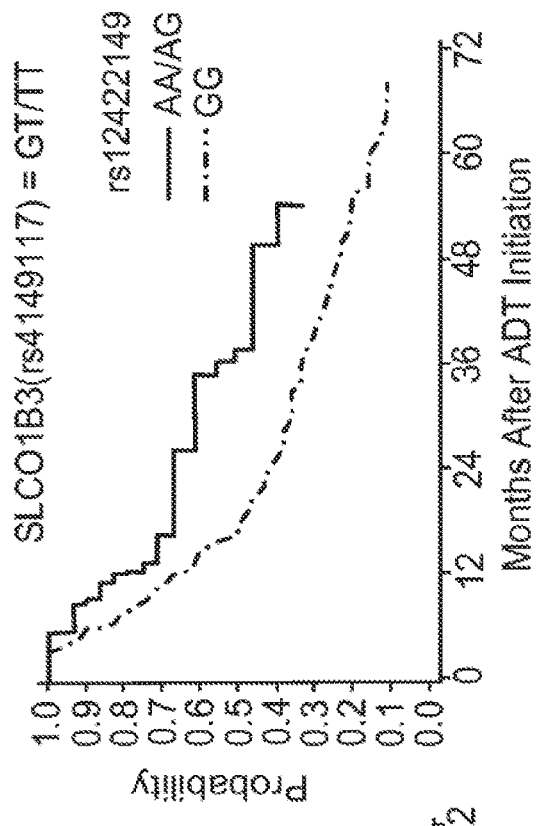
FIGS. 4A-4H are Kaplan-Meier curves of time to progression during androgen deprivation therapy, stratified by: genotype at rs12422149 (SLCO2B1) and rs4149117 (SLCO1B3) (FIGS. 4A and 4B); genotype at rs1789693 (SLCO2B1) and rs4149117 (SLCO1B3) (FIGS. 4C and 4D); genotype at rs1077858 (SLCO2B1) and rs4149117 (SLCO1B3) (FIGS. 4E and 4F); ≤1, 2, or 3 unfavorable genotype(s) of the three SLCO2B1 SNPs and rs4149117 (SLCO1B3) (FIGS. 4G and 4H).
Figure 4C:
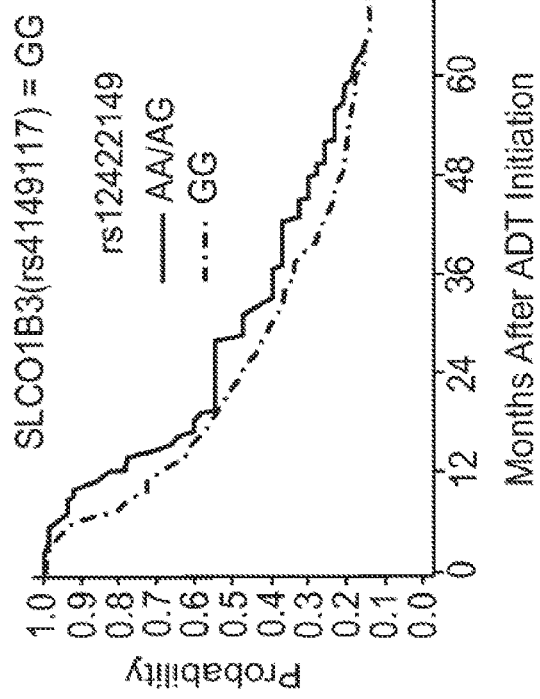
Figure 4B:
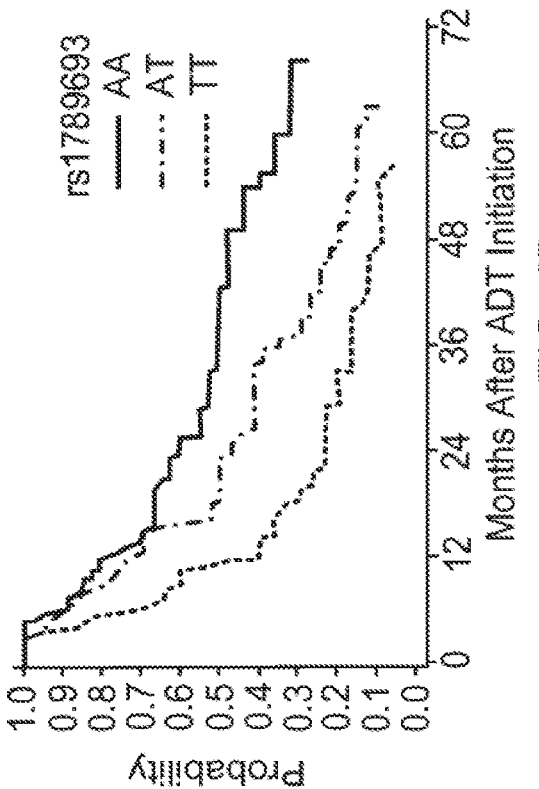
Figure 4D:
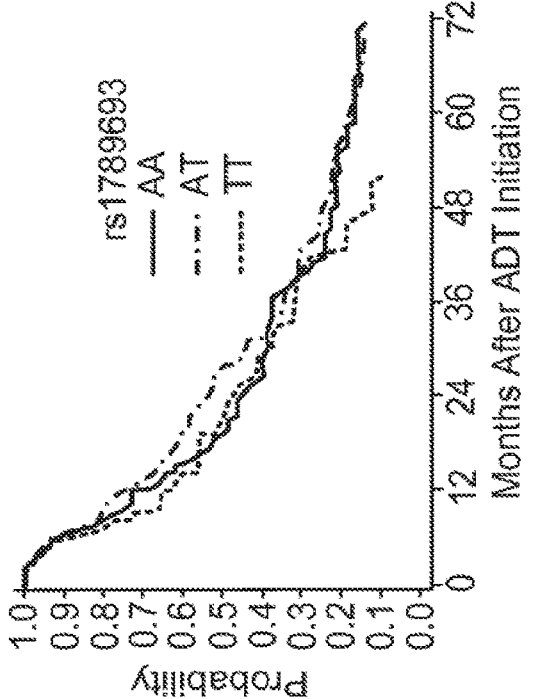
Figure 4E:
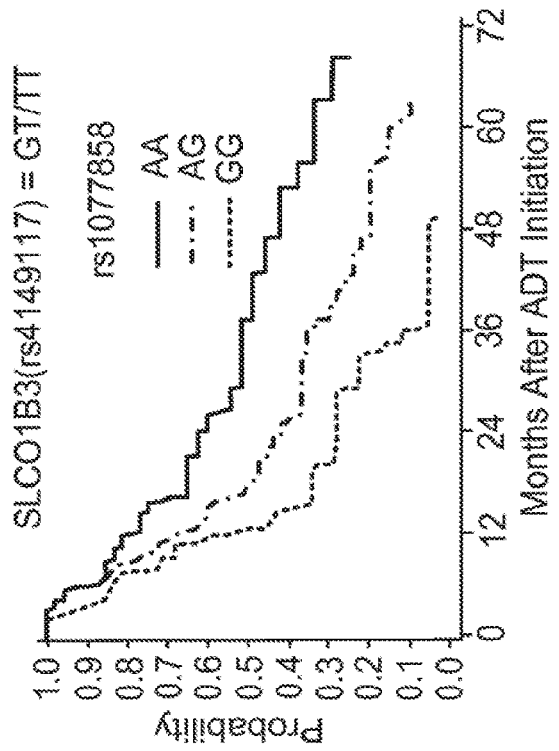
Figure 4G:
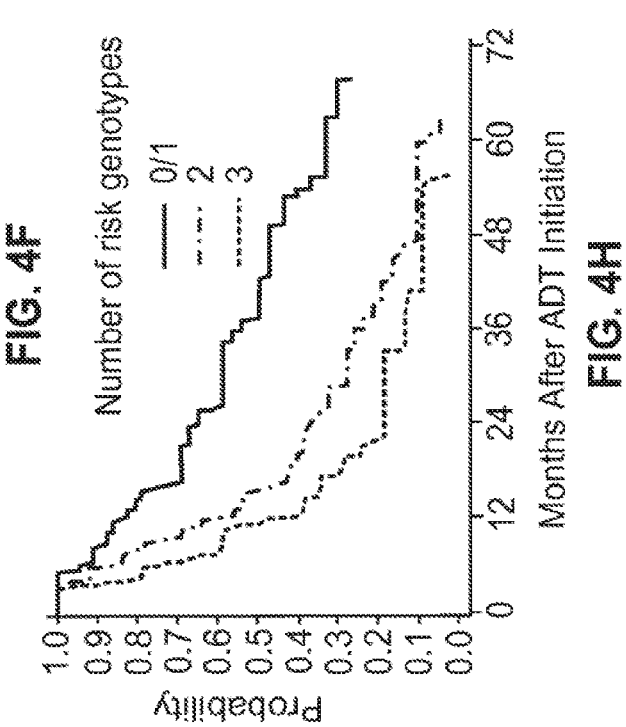
Figure 4F:
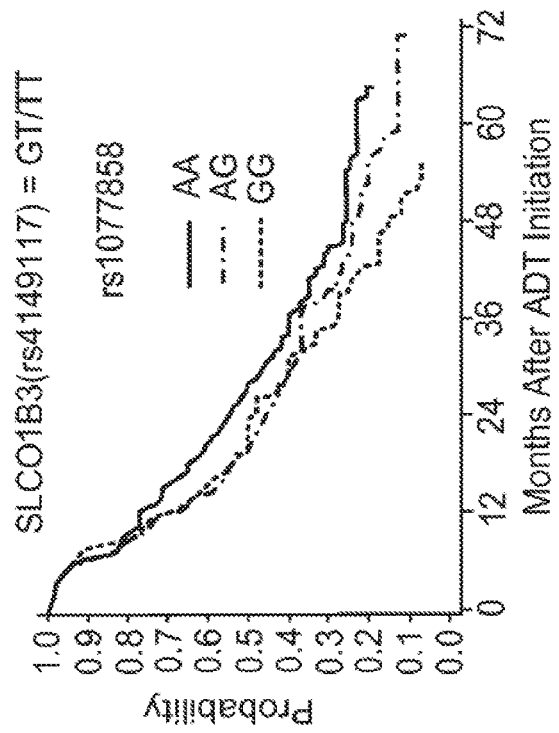
Figure 4H:
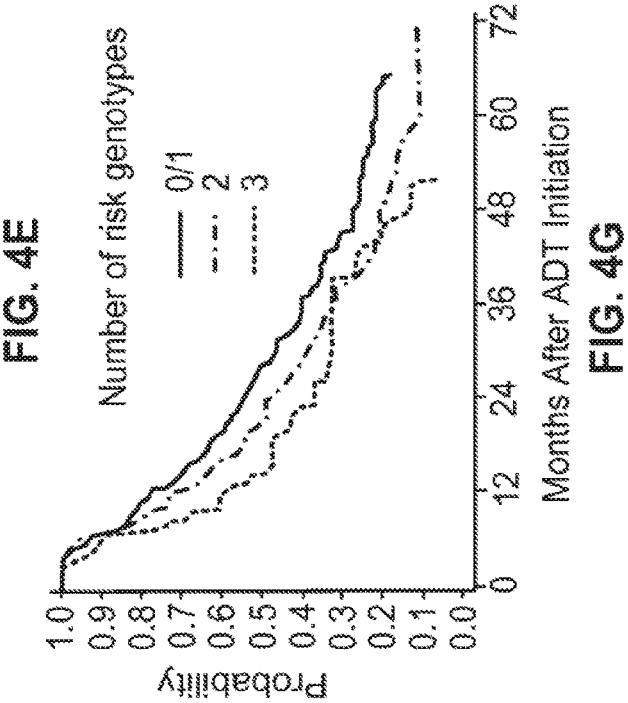

The growth efficiency was compared of wild type LNCaP and LAPC4 and cell lines that were transfected with different SLCO2B1 variants in the presence or absence of 100 µM DHEAS. As shown in FIG. 3E, DHEAS increased the growth rate of LNCaP by about 1.4-fold. In the presence of DHEAS, the growth efficiency of LNCaP cells transfected with SLCO2B1-312Gln increased 2.5-fold, while the growth efficiency of LNCaP cells transfected with SLCO2B1-312Arg only increased 2.0-fold (P<0.05). Similar results were also found in LAPC-4 cells (FIG. 3F). In sum, the data demonstrated that the uptake of DHEAS activates AR signaling and promotes cell growth.

Example 5

Gene-Gene Interaction Between SLCO2B1 and SLCO1B3 Polymorphisms

While a three months shorter median TTP during ADT was observed in patients carrying the SLCO1B3 risk alleles (rs4149117 T allele or rs7311358 G allele) compared to patients with favorable genotypes (rs4149117 GG or rs7311358 AA), these two SNPs alone did not have a statistically significant association with TTP on ADT (Table 4). Since both SLCO2B1 and SLCO1B3 are involved in transport of androgens (DHEAS and testosterone) into CaP cells, it is possible that the impact of SLCO1B3 variants on TTP in ADT may be revealed in patients with different SLCO2B1 alleles. Thus, it was investigated if the SLCO1B3 variants interacted with the three SLCO2B1 SNPs.

As shown in Table 5 and FIG. 4, the association of TTP on ADT with SLCO2B1 polymorphisms was significantly modified by the genotype of SLCO1B3-rs4149117 ($P_{interaction}$=0.24, 0.02 and 0.09, respectively). Men with both SLCO1B3-rs4149117 GT/TT and SLCO2B1-rs12422149GG, or -rs1789693 TT or -rs1077858 GG genotypes progressed more rapidly than men with either rs4149117 GT/TT genotype coupled with the favorable alleles SLCO2B1 (HR and 95% CI: 1.72(1.04; 2.85), 2.90 (1.75; 4.79) and 2.95(1.65; 5.28), respectively). The interaction remained significant in multivariable models adjusted for clinical factors. The additive effect of the combinations of SLCO2B1 three alleles was also further enhanced by SLCO1B3 SNPs ($P_{interaction}$=0.041). As shown in Table 5 and FIGS. 4G and 4H, compared with men with one or zero risk allele, the HR (95% CI) for three risk alleles of SLCO2B1 was 3.57 (2.03; 6.26) in patients with the SLCO1B3-rs4149117 GT/TT genotypes and only 1.60 (0.99; 2.58) in patients carrying the rs4149117 GG genotype. A similar trend was observed for the interaction between SLCO2B1 alleles and SLCO1B3 rs7311358, which is in strong LD with the SLCO1B3 rs4149117 polymorphism. These results demonstrated that SLCO1B3 genotypes could significantly modify rates of disease progression, specifically for those patients who carry the SLCO2B1 risk alleles.

TABLE 5

Gene-Gene interaction between SLCO2B1 and SLCO1B3 SNPs on TTP during ADT

| SLCO2B1 genotype | SLCO1B3 rs4149117 | | | | P-value* (Interaction) |
|---|---|---|---|---|---|
| | GG | | GT/TT | | |
| | N | HR (95% CI) | N | HR (95% CI) | |
| rs12422149 | | | | | |
| AA/AG | 64 | 1.00 (reference) | 34 | 1.00 (reference) | 0.237 |
| GG | 304 | 1.21 (0.88,1.67) | 128 | 1.72 (1.04,2.85) | |
| rs1789693 | | | | | |
| AA | 153 | 1.00 (reference) | 59 | 1.00 (reference) | 0.022 |
| AT | 158 | 0.91 (0.70,1.17) | 67 | 1.68 (1.07,2.65) | |
| TT | 47 | 1.20 (0.80,1.81) | 33 | 2.90 (1.75,4.79) | |
| rs1077858 | | | | | |
| AA | 138 | 1.00 (reference) | 49 | 1.00 (reference) | 0.092 |
| AG | 146 | 1.17(0.89,1.55) | 79 | 1.64 (1.06,2.55) | |
| GG | 51 | 1.29 (0.89,1.87) | 22 | 2.95 (1.65,5.28) | |
| No. of risk genotype | | | | | |
| ≤1 | 167 | 1.00 (reference) | 67 | 1.00 (reference) | 0.041 |
| 2 | 139 | 1.22 (0.93,1.59) | 64 | 2.38 (1.53,3.70) | |
| 3 | 29 | 1.60 (0.99,2.58) | 20 | 3.57 (2.03,6.26) | |

*Wald Chi-square test for interaction from Cox regression

Other Embodiments

While the invention has been described in conjunction with the foregoing detailed description and examples, the foregoing description and examples are intended to illustrate and not to limit the scope of the invention, which is defined by the scope of the appended claims. Other aspects, advantages, and modifications are within the scope of the claims.

What is claimed is:

1. A method of therapy of a subject with prostate cancer, the method comprising:
assaying using a biological sample from the subject the genotypes of two or more SLCO2B1 single nucleotide polymorphisms (SNP) selected from the group consisting of rs12422149, rs1789693, and rs1077858, and one or more SLCO2B3 SNPs selected from the group consisting of rs4149117 and rs7311358;
based on the assaying, detecting that the subject does not have two or more SLCO2B1 SNP genotypes selected from the group consisting of rs12422149 (GG), rs1789693 (TT), and rs1077858 (AG/GG) and does not have one or more SLCO2B3 SNP genotypes selected from the group consisting of rs4149117 (GT/TT) and rs7311358 (AG/GG); and then performing, as the therapy, a treatment for prostate cancer which comprises one of the following (1) androgen-deprivation therapy (ADT), (2) ketoconazole treatment, and (3) abiraterone treatment.

2. The method of claim 1, wherein the biological sample is a blood or tissue sample.

3. The method of claim 2, wherein the biological sample is a blood sample that is a peripheral blood sample.

4. The method of claim 2, wherein the biological sample is a tissue sample that is a mucosal scraping sample of the lining of the mouth or a prostate tissue sample.

5. The method of claim 1, wherein the subject is human.

6. The method of claim 1, wherein the treatment is ADT.

7. The method of claim 1, wherein the assaying is performed by at least one method selected from the group consisting of sequencing, allele-specific hybridization, allele-specific restriction digests, mutation specific polymerase chain reactions (MSPCR), single-stranded conformational polymorphism (SSCP) detection, denaturing high performance liquid chromatography (DHPLC), and infrared matrix-assisted laser desorption/ionization (IR-MALDI) mass spectrometry.

8. A method of therapy of a subject with prostate cancer, the method comprising:
performing, as the therapy, a treatment for prostate cancer which comprises one of the following (1) androgen-deprivation therapy (ADT), (2) ketoconazole treatment, and (3) abiraterone treatment,
wherein a biological sample from the subject has been previously tested and identified as not having two or more SLCO2B1 SNP genotypes selected from the group consisting of rs12422149 (GG), rs1789693 (TT), and rs1077858 (AG/GG) and not having one or more SLCO2B3 SNP genotypes selected from the group consisting of rs4149117 (GT/TT) and rs7311358 (AG/GG).

9. The method of claim 8, wherein the biological sample is a blood or tissue sample.

10. The method of claim 9, wherein the biological sample is a blood sample that is a peripheral blood sample.

11. The method of claim 9, wherein the biological sample is a tissue sample that is a mucosal scraping sample of the lining of the mouth or a prostate tissue sample.

12. The method of claim 8, wherein the treatment is ADT.

13. The method of claim 8, wherein the biological sample from the subject has previously been tested and identified as not having two or more SLCO2B1 SNP genotypes selected from the group consisting of rs12422149 (GG), rs1789693 (TT), and rs1077858 (AG/GG) and not having one or more SLCO2B3 SNP genotypes selected from the group consisting of rs4149117 (GT/TT) and rs7311358 (AG/GG) by at least one method selected from the group consisting of sequencing, allele-specific hybridization, allele-specific restriction digests, mutation specific polymerase chain reactions (MSPCR), single-stranded conformational polymorphism (SSCP) detection, denaturing high performance liquid chromatography (DHPLC), and infrared matrix-assisted laser desorption/ionization (IR-MALDI) mass spectrometry.

14. A method of therapy of a subject with prostate cancer, the method comprising:
performing, as the therapy, a treatment for prostate cancer which comprises one of the following (1) androgen-deprivation therapy (ADT), (2) ketoconazole treatment, and (3) abiraterone treatment,
wherein a biological sample from the subject has been previously tested and identified as having one or more SLCO2B1 SNP genotypes selected from the group consisting of rs12422149 (AA/AG), rs1789693 (AA/

AT), and rs1077858 (AA) and having one or more SLCO2B3 SNP genotypes selected from the group consisting of rs4149117 (GG) and rs7311358 (AA).

15. The method of claim 14, wherein the biological sample is a blood or tissue sample.

16. The method of claim 15, wherein the biological sample is a blood sample that is a peripheral blood sample.

17. The method of claim 15, wherein the biological sample is a tissue sample that is a mucosal scraping sample of the lining of the mouth or a prostate tissue sample.

18. The method of claim 14, wherein the subject is human.

19. The method of claim 14, wherein the treatment is ADT.

20. The method of claim 14, wherein the biological sample from the subject has previously been tested and identified as not having two or more SLCO2B1 SNP genotypes selected from the group consisting of rs12422149 (GG), rs1789693 (TT), and rs1077858 (AG/GG) and not having one or more SLCO2B3 SNP genotypes selected from the group consisting of rs4149117 (GT/TT) and rs7311358 (AG/GG) by at least one method selected from the group consisting of sequencing, allele-specific hybridization, allele-specific restriction digests, mutation specific polymerase chain reactions (MSPCR), single-stranded conformational polymorphism (SSCP) detection, denaturing high performance liquid chromatography (DHPLC), and infrared matrix-assisted laser desorption/ionization (IR-MALDI) mass spectrometry.

21. The method of claim 5, wherein the human is a man.

22. The method of claim 18, wherein the human is a man.

* * * * *

SEQUENCE LISTING

```
<160> NUMBER OF SEQ ID NOS: 2

<210> SEQ ID NO 1
<211> LENGTH: 35
<212> TYPE: DNA
<213> ORGANISM: Artificial Sequence
<220> FEATURE:
<223> OTHER INFORMATION: oligonucleotide

<400> SEQUENCE: 1
tgagcttcag tttcggcaaa aggtcttagc agtca                              35

<210> SEQ ID NO 2
<211> LENGTH: 35
<212> TYPE: DNA
<213> ORGANISM: Artificial Sequence
<220> FEATURE:
<223> OTHER INFORMATION: oligonucleotide

<400> SEQUENCE: 2
tgactgctaa gaccttttgc cgaaactgaa gctca                              35
```